US006410237B1

(12) United States Patent
Brewer et al.

(10) Patent No.: US 6,410,237 B1
(45) Date of Patent: Jun. 25, 2002

(54) DNA ENCODING CANINE VON WILLEBRAND FACTOR AND METHODS OF USE

(75) Inventors: George J. Brewer, Ann Arbor; Patrick J. Venta, Pinckney; Vilma Yuzbasiyan-Gurkan, Ann Arbor; William D. Schall, Williamston, all of MI (US)

(73) Assignees: Board of Trustees operating Michigan State University, East Lansing; The Regents of the University of Michigan, Ann Arbor, both of MI (US)

( * ) Notice: Subject to any disclaimer, the term of this patent is extended or adjusted under 35 U.S.C. 154(b) by 0 days.

(21) Appl. No.: 09/432,451

(22) Filed: Nov. 2, 1999

Related U.S. Application Data

(63) Continuation of application No. 08/896,449, filed on Jul. 18, 1997, now Pat. No. 6,040,143.

(51) Int. Cl.$^7$ .............................. C12P 19/34; C12N 1/20; C12N 5/00; C07H 19/00; C07H 21/04

(52) U.S. Cl. ..................... 435/6; 435/91.1; 435/91.2; 435/252.3; 435/325; 536/22.1; 536/23.5; 536/24.31; 536/24.33

(58) Field of Search ........................... 536/22.1, 23.5, 536/24.31, 24.33; 435/325, 252.3, 6, 91.1, 91.2

(56) References Cited

FOREIGN PATENT DOCUMENTS

| EP | 197592 | 10/1986 | ........... C12N/15/00 |
|---|---|---|---|
| WO | WO 96/15262 | 5/1996 | ........... C12Q/1/68 |
| WO | WO 98/03683 | 1/1998 | ........... C12Q/1/68 |

OTHER PUBLICATIONS

Avgeris, S. et al. "Plasma von Willebrand Factor Concentration and Thyroid Function in Dogs" *JAVMA* 196:921–92 (1990).
Bakhshi, M.R. et al. Sequencing of the Primary Adhesion Domain of Bovine von Willebrand Factor: *Biochem. Biophys. Acta* 1132:325–28 (1992).
Benson, R.E. et al. "Efficiency and Precision of Electroimmunoassay for Canine Factor VIII–Related Antigen" *Am. J. Vet. Res.* 44:399–403 (1983).
Bergenhem, N.C.H. et al. "Mutation Creates an Open Reading Frame within the 5' Untranslated Region of Macaque Erythrocyte Carbonic Anhydrase (CA) I mRNA that Suppresses CA I Expression and Supports the Scanning Model for Translation" *Proc. Natl. Acad. Sci. USA* 89:8789–8802 (1992).
Bloom, A.L. "Von Willebrand Factor: Clinical Features of Inherited and Acquired Disorders" *Mayo Clin. Proc.* 66:743–51 (1991).

Bonthron, D. et al. "Nucleotide Sequence of Pre–Pro–von Willebrand Factor cDNA" *Nucleic Acids Res.* 14:7125–27 (1986).
Brinkhous, K.M. et al. "Pathophysiology of Platelet–Aggregating von Willebrand Factor: Applications of the Venom Coagglutinin vWF Assay" *Ann. New York Acad. Sci.* 370:191–204 (1981).
Brooks, M. "Clinical Features of Canine von Willebrand's Disease" *Proc. 9$^{th}$ ACVIM Forum*: 89–91 (1991).
Brooks, M. "Management of Canine von Willebrand's Disease" *Probl. In Vet. Med.* 4:636–46 (1992).
Brooks, M. et al. "Epidemiologic Features of von Willebrand's Disease in Doberman Pinschers, Scottish Terriers, and Shetland Sheepdogs: 260 Cases (1984–1988)" *JAVMA* 200:1123–27 (1992).
Dodds, W.J. "Von Willebrand's Disease in Dogs" *Mod. Vet. Pract.* 618–686 (1984).
Ginsberg, D. et al. "Molecular Genetics of von Willebrand Disease" *Blood* 79:2507–19 (1992).
Janel, N. et al. "Comparison of the 5'–Flanking Sequences of the Human and Bovine von Willebrand Factor–Encoding Genes Reveals Alternation of Highly Homologous Domains with Species–Specific *Alu* –Type Repeats" *Gene* 167:291–95 (1995).
Johnson, G.S. et al. "A Bleeding Disease (von Willebrand's Disease) in a Chesapeake Bay Retriever" *JAVMA* 176:1261–63 (1980).
Kraus, K.H. et al. "Effect of Desmopressin Acetate on Bleeding Times and Plasma von Willebrand Factor in Doberman Pinscher Dogs with von Willebrand's Disease" *Vet. Surg.* 18:103–09 (1989).
Lankhof, H. et al. "Role of the Glycoprotein lb–Binding A1 Repeat and the RGD Sequence in Platelet Adhesion to Human Recombinant von Willebrand Factor" *Blood* 86:1035–42 (1995).
Lavergne, J.M. et al. "Primary Structure of the Factor VIII Binding Domain of Human, Porcine and Rabbit von Willebrand Factor" *Biochem. Biophys. Res. Commun.* 194:1019–24 (1993).
Mancuso, D.J. et al. "Human von Willebrand Factor Gene and Pseudogene: Structural Analysis and Differentiation by Polymerase Chain Reaction" *Biochemistry* 30:253–69 (1991).

(List continued on next page.)

*Primary Examiner*—Stephanie Zitomer
*Assistant Examiner*—Joyce Tung
(74) *Attorney, Agent, or Firm*—DeAnn F. Smith, Esq.; Lahive & Cockfield, LLP

(57) ABSTRACT

The complete sequence of the canine von Willebrand Factor cDNA and deduced amino acid sequence is provided. The mutation which causes von Willebrand's Disease in Scottish Terriers, a single base deletion in exon 4, has also been determined. Methods for detecting carriers of the defective vWF gene are also provided.

15 Claims, 9 Drawing Sheets

OTHER PUBLICATIONS

Mancuso, D.J. et al. "An Homologous Canine von Willebrand and Factor Binding Domain for Glycoprotein lb" *Thromb. Haemost.* 69:980–1576 (1993).

Maniatis, T. et al. *Molecular Cloning: A Laboratory Manual*, Cold Spring Harbor Laboratory Press, Cold Spring, NY: 387–89 (1982).

Mansell, P.D. et al. "Changes in Factor VIII Activity and von Willebrand Factor Antigen Concentration with Age in Dogs" *Br. Vet. J.* 148:329–37 (1992).

Meyer, D. et al. "von Willebrand Factor: Structure and Function" *Thromb. Haemost.* 70:99–104 (1993).

O'Brien, P.J. et al. "Use of a DNA–Based Test for the Mutation Associated with Porcine Stress Syndrome (Malignant Hyperthermia) in 10,000 Breeding Swine" *JAVMA* 203:842–51 (1993).

Panciera, D.L. et al. "Plasma von Willebrand Factor Antigen Concentration in Dogs with Hypothyroidism" *JAVMA* 205:1550–53 (1994).

Porter, C.A. et al. "Evidence of Mammalian Phylogeny from Sequences of Exon 28 of the von Willebrand Factor Gene" *Mol. Phylogenet. Evol.* 5:89–101 (1996).

Read, M.S. et al. "Venom Coagglutinin for Detection of von Willebrand Factor Activity in Animal Plasmas" *J. Lab. Clin. Med.* 101:74–82 (1983).

Richards, B. et al. "Multiplex PCR Amplification from the CFTR Gene Using DNA Prepared from Buccal Brushes/Swabs" *Human Molec. Genet.* 2:159–63 (1992).

Rosborough, T.K. et al. "Measurement of Canine von Willebrand Factor Using Ristocetin and Polybrene" *J. Lab. Clin. Med.* 96:47–56 (1980).

Rudolph, J.A. et al. "Periodic Paralysis in Quarter Horses: a Sodium Channel Mutation Disseminated by Selective Breeding" *Nat. Genet.* 2:144–47 (1992).

Ruggeri, Z.M. et al. "von Willebrand Factor" *FASEB J.* 7:308–16 (1993).

Sadler, J.E. et al. "Commentary: A New Classification for von Willebrand Disease" *Blood* 84:676–79 (1994).

Sambrook, J. et al. "Identification of cDNA Clones of Interest" *Molecular Cloning: A Laboratory Manual*, Second Edition, vol. 2, Cold Spring Harbor Laboratory Press, Cold Spring, NY : 8.46–8.47 (1989).

Shibuya, H. et al. "A Polymorphic $(AGGATT)_n$ Tandem Repeat in an Intron of the Canine von Willebrand Factor Gene" *Anim. Genet.* 25:122 (1994).

Shuster, D.E. et al. "Identification and Prevalence of a Genetic Defect that Causes Leukocyte Adhesion Deficiency in Holstein Cattle" *Proc. Natl. Acad. Sci. USA* 89:9225–29 (1992).

Slappendel, R.J. "von Willebrand's Disease in Dutch Kooiker Dogs" *Vet–Q* 17:S21–S22 (1995).

Stirling, Y. et al. "Haemostasis in Normal Pregnancy" *Thromb. Haemost.* 52:176–82 (1984).

Stokol, T. et al. "Stability of von Willebrand Factor and Factor VIII in Canine Cryoprecipitate Under Various Conditions of Storage" *Res. Vet. Sci.* 59:152–55 (1995).

Strauss, H.S. et al. Elevation of Factor VIII (Antihemophilic Factor) During Pregnancy in Normal Persons and in a Patient with von Willebrand's Disease *New Eng. J. Med.* 269:1251–52 (1963).

Turrentine, M.A. et al. "Plasma from Donor Dogs, Pretreated with DDVAP, Transfused into German Shorthair Pointer with Type II von Willebrand's Disease" *Vet. Clin. North Am. Small Anim. Pract.* 18:275 (1988).

Venta, P.J. et al. "Gene–Specific Universal Mammalian Sequence–Tagged Sites: Application to the Canine Genome" *Biochem. Genet.* 34:321–41 (1996).

Verweij, C.L. et al. "Expression of Variant von Willebrand Factor (vWF) cDNA in Heterologous Cells: Requirement of the Pro–polypeptide in vWF Multimer Formation" *EMBO J.* 6:2885–90 (1987).

Wise, R.J. et al. "The Propeptide of von Willebrand Factor Independently Mediates the Assembly on von Willebrand Multimers" *Cell* 52:229–36 (1988).

FIGURE 1A

```
   1 CATTAANAGG TCCTGGCTGG GAGCTTTTTT TTGGGACCAG CACTCCATGT TCAAGGGCAA
  61 ACAGGGGCCA ATTAGGATCA ATCTTTTTTC TTTCTTTTTT TAAAAAAAAA AATTCTTCCC
 121 ACTTTGCACA CGGACAGTAG TACATACCAG TAGCTCTCTG CGAGGACGGT GATCACTAAT
 181 CATTTCTCCT GCTTCGTGGC AGATGAGTCC TACCAGACTT GTGAGGGTGC TGCTGGCTCT
 241 GGCCCTCATC TTGCCAGGGA AACTTTGTAC AAAAGGGACT GTTGGAAGGT CATCGATGGC
 301 CCGATGTAGC CTTCTCGGAG GTGACTTCAT CAACACCTTT GATGAGAGCA TGTACAGCTT
 361 TGCGGGAGAT TGCAGTTACC TCCTGGCTGG GGACTGCCAG GAACACTCCA TCTCACTTAT
 421 CGGGGGTTTC CAAAATGACA AAGAGTGAG CCTCTCCGTG TATCTCGGAG AATTTTTCGA
 481 CATTCATTTG TTTGTCAATG GTACCATGCT GCAGGGGACC CAAAGCATCT CCATGCCCTA
 541 CGCCTCCAAT GGGCTGTATC TAGAGGCCGA GGCTGGCTAC TACAAGCTGT CCAGTGAGGC
 601 CTACGGCTTT GTGGCCAGAA TTGATGGCAA TGGCAACTTT CAAGTCCTGC TGTCAGACAG
 661 ATACTTCAAC AAGACCTGTG GGCTGTGTGG CAACTTTAAT ATCTTTGCTG AGGATGACTT
 721 CAAGACTCAA GAAGGGACGT TGACTTCGGA CCCCTATGAC TTTGCCAACT CCTGGGCCCT
 781 GAGCAGTGGG GAACAACGGT GCAAACGGGT GTCCCCTCCC AGCAGCCCAT GCAATGTCTC
 841 CTCTGATGAA GTGCAGCAGG TCCTGTGGGA GCAGTGCCAG CTCCTGAAGA GTGCCTCGGT
 901 GTTTGCCCGC TGCCACCCGC TGGTGGACCC TGAGCCTTTT GTCGCCCTGT GTGAAAGGAC
 961 TCTGTGCACC TGTGTCCAGG GGATGGAGTG CCCTTGTGCG GTCCTCCTGG AGTACGCCCG
1021 GGCCTGTGCC AGCAGGGGA TTGTCTTGTA CGGCTGGACC GACCACAGCG TCTGCCGACC
1081 AGCATGCCCT GCTGGCATGG AGTACAAGGA GTGCGTGTCC CCTTGCACCA GAACTTGCCA
1141 GAGCCTTCAT GTCAAAGAAG TGTGTCAGGA GCAATGTGTA GATGGCTGCA GCTGCCCCGA
1201 GGGCCAGCTC CTGGATGAAG CCACTGCGT GGGAAGTGCT GAGTGTTCCT GTGTGCATGC
1261 TGGGCAACGG TACCCTCCGG CGCCTCCCT CTTACAGGAC TGCCACACCT GCATTTGCCG
1321 AAATAGCCTG TGGATCTGCA GCAATGAAGA ATGCCCAGGC GAGTGTCTGG TCACAGGACA
1381 GTCCCACTTC AAGAGCTTCG ACAACAGGTA CTTCACCTTC AGTGGGGTCT GCCACTACCT
1441 GCTGGCCCAG GACTGCCAGG ACCACACATT CTCTGTTGTC ATAGAGACTG TCCAGTGTGC
1501 CGATGACCTG GATGCTGTCT GCACCCGCTC GGTCACCGTC CGCCTGCCTG ACATCACAA
1561 CAGCCTTGTG AAGCTGAAGA ATGGGGGAGG AGTCTCCATG GATGGCCAGG ATATCCAGAT
1621 TCCTCTCCTG CAAGGTGACC TCGCATCCA GCACACCGTG ATGGCCTCCG TGCGCCTCAG
1681 CTACGGGGAG GACCTGCAGA TGGATTCGGA CGTCCGGGGC AGGCTACTGG TGACGCTGTA
1741 CCCCGCCTAC GCGGGGAAGA CGTGCGGCCG TGCGGGAAC TACAACGGCA ACCGGGGGGA
1801 CGACTTCGTG ACGCCCGCAG GCCTGGCGGA GCCCTGGTG GAGGACTTCG GAACGCCTG
1861 GAAGCTGCTC GGGGCCTGCG AGAACCTGCA GAAGCAGCAC CGCGATCCCT GCAGCCTCAA
1921 CCCGCGCCAG GCCAGGTTTG CGGAGGAGGC GTGCGCGCTG CTGACGTCCT CGAAGTTCGA
1981 GCCCTGCCAC CGAGCGGTGG GTCCTCAGCC CTACGTGCAG AACTGCCTCT ACGACGTCTG
2041 CTCCTGCTCC GACGGCAGAG ACTGTCTTTG CAGCGCCGTG GCCAACTACG CCGCAGCCGT
2101 GGCCCGGAGG GGCGTGCACA TCGCGTGGCG GGAGCCGGGC TTCTGTGCGC TGAGCTGCCC
2161 CCAGGGCCAG GTGTACCTGC AGTGTGGGAC CCCCTGCAAC ATGACCTGTC TCTCCCTCTC
2221 TTACCCGGAG GAGGACTGCA ATGAGGTCTG CTTGGAAAGC TGCTTCTCCC CCCAGGGCT
2281 GTACCTGGAT GAGAGGGAG ATTGTGTGCC CAAGGCTCAG TGTCCCTGTT ACTATGATGG
2341 TGAGATCTTT CAGCCCGAAG ACATCTTCTC AGACCATCAC ACCATGTGCT ACTGTGAGGA
2401 TGGCTTCATG CACTGTACCA CAAGTGGAGG CCTGGGAAGC CTGCTGCCCA ACCCGGTGCT
2461 CAGCAGCCCC CGGTGTCACC GCAGCAAAAG GAGCCTGTCC TGTCGGCCCC CCATGGTCAA
2521 GTTGGTGTGT CCCGCTGATA ACCCGAGGGC TGAAGGACTG GAGTGTGCCA AAACCTGCCA
2581 GAACTATGAC CTGCAGTGCA TGAGCACAGG CTGTGTCTCC GGCTGCCTCT GCCCGCAGGG
2641 CATGGTCCGG CATGAAAACA GGTGTGTGGC GCTGGAAAGA TGTCCCTGCT TCCACCAAGG
2701 CCAAGAGTAC GCCCCAGGAG AAACCGTGAA AATTGACTGC AACACTTGTG TCTGTCGGGA
2761 CCGGAAGTGG AACCTGCACAG ACCATGTGTG TGATGCCACT TGCTCTGCCA TCGGCATGGC
2821 GCACTACCTC ACCTTCGACG GACTCAAGTA CCTGTTCCCT GGGGAGTGCC AGTATGTTCT
2881 GGTGCAGGAT TACTGCGGCA GTAACCCTGG GACCTTACGG ATCCTGGTGG GAACGAGGG
2941 GTGCAGCTAC CCCTCAGTGA AATGCAAGAA GCGGGTCACC ATCCTGGTGG AAGGAGGAGA
3001 GATTGAACTG TTTGATGGGG AGGTGAATGT GAAGAAACCC ATGAAGGATG AGACTCACTT
3061 TGAGGTGGTA GAGTCTGGTC AGTACGTCAT TCTGCTGCTG GGCAAGGCAC TCTCTGTGGT
3121 CTGGGACCAC CGCCTGAGCA TCTCTGTGAC CCTGAAGCGG ACATACCAGG AGCAGGTGTG
```

FIGURE 1B

```
3181 TGGCCTGTGT GGGAATTTTG ATGGCATCCA GAACAATGAT TTCACCAGCA GCAGCCTCCA
3241 AATAGAAGAA GACCCTGTGG ACTTTGGGAA TTCCTGGAAA GTGAACCCGC AGTGTGCCGA
3301 CACCAAGAAA GTACCACTGG ACTCATCCCC TGCCGTCTGC CACAACAACA TCATGAAGCA
3361 GACGATGGTG GATTCCTCCT GCAGGATCCT CACCAGTGAT ATTTTCCAGG ACTGCAACAG
3421 GCTGGTGGAC CCTGAGCCAT TCCTGGACAT TTGCATCTAC GACACTTGCT CCTGTGAGTC
3481 CATTGGGGAC TGCACCTGCT TCTGTGACAC CATTGCTGCT TACGCCCACG TCTGTGCCCA
3541 GCATGGCAAG GTGGTAGCCT GGAGGACAGC CACATTCTGT CCCCAGAATT GCGAGGAGCG
3601 GAATCTCCAC GAGAATGGGT ATGAGTGTGA GTGGCGCTAT AACAGCTGTG CCCCTGCCTG
3661 TCCCATCACG TGCCAGCACC CCGAGCCACT GGCATGCCCT GTACAGTGTG TTGAAGGTTG
3721 CCATGCGCAC TGCCCTCCAG GGAAAATCCT GGATGAGCTT TTGCAGACCT GCATCGACCC
3781 TGAAGACTGT CCTGTGTGTG AGGTGGCTGG TCGTCGCTTG CCCCAGGAA AGAAAATCAT
3841 CTTGAACCCC AGTGACCCTG AGCACTGCCA AATTTGTAAT TGTGATGGTG TCAACTTCAC
3901 CTGTAAGGCC TGCAGAGAAC CCGAAGTGT TGTGGTGCCC CCACAGATG GCCCCATTGG
3961 CTCTACCACC TCGTATGTGG AGGACACGTC GGAGCCGCCC CTCCATGACT TCCACTGCAG
4021 CAGGCTTCTG GACCTGGTTT TCCTGCTGGA TGGCTCCTCC AAGCTGTCTG AGGACGAGTT
4081 TGAAGTGCTG AAGGTCTTTG TGGTGGGTAT GATGGAGCAT CTGCACATCT CCCAGAAGCG
4141 GATCCGCGTG GCTGTGGTGG AGTACCACGA CGGCTCCCAC GCCTACATCG AGCTCAAGGA
4201 CCGGAAGCGA CCCTCAGAGC TGCGGCGCAT CACCAGCCAG GTGAAGTACG CGGGCAGCGA
4261 GGTGGCCTCC ACCAGTGAGG TCTTAAAGTA CACGCTGTTC CAGATCTTTG GCAAGATCGA
4321 CCGCCCGGAA GCGTCTCGCA TTGCCCTGCT CCTGATGGCC AGCCAGGAGC CCTCAAGGCT
4381 GGCCCGGAAT TTGGTCCGCT ATGTGCAGGG CCTGAAGAAG AAGAAAGTCA TTGTCATCCC
4441 TGTGGGCATC GGGCCCCACG CCAGCCTTAA GCAGATCCAC CTCATAGAGA AGCAGGCCCC
4501 TGAGAACAAG GCCTTTGTGT TCAGTGGTGT GGATGAGTTG GAGCAGCGAA GGGATGAGAT
4561 TATCAACTAC CTCTGTGACC TTGCCCCCGA AGCACCTGCC CCTACTCAGC ACCCCCCAAT
4621 GGCCCAGGTC ACGGTGGGTT CGGAGCTGTT GGGGGTTTCA TCTCCAGGAC CCAAAAGGAA
4681 CTCCATGGTC CTGGATGTGG TGTTTGTCCT GGAAGGGTCA GACAAAATTG GTGAGGCCAA
4741 CTTTAACAAA AGCAGGGAGT TCATGGAGGA GGTGATTCAG CGGATGGACG TGGGCCAGGA
4801 CAGGATCCAC GTCACAGTGC TGCAGTACTC GTACATGGTG ACCGTGGAGT ACACCTTCAG
4861 CGAGGCGCAG TCCAAGGGCG AGGTCCTACA GCAGGTGCGG GATATCCGAT ACCGGGGTGG
4921 CAACAGGACC AACACTGGAC TGGCCCTGCA ATACCTGTCC GAACACAGCT CTCGGTCAG
4981 CCAGGGGGAC CGGGAGCAGG TACCTAACCT GGTCTACATG GTCACAGGAA ACCCCGCTTC
5041 TGATGAGATC AAGCGGATGC CTGGAGACAT CCAGGTGGTG CCCATCGGGG TGGGTCCACA
5101 TGCCAATGTG CAGGAGCTGG AGAAGATTGG CTGGCCCAAT GCCCCATCC TCATCCATGA
5161 CTTTGAGATG CTCCCTCGAG AGGCTCCTGA TCTGGTGCTA CAGAGGTGCT GCTCTGGAGA
5221 GGGGCTGCAG ATCCCCACCC TCTCCCCAC CCCAGATTGC AGCCAGCCCC TGGATGTGGT
5281 CCTCCTCCTG GATGGCTCTT CCAGCATTCC AGCTTCTTAC TTTGATGAAA TGAAGAGCTT
5341 CACCAAGGCT TTTATTTCAA GAGCTAATAT AGGGCCCCGG CTCACTCAAG TGTCGGTGCT
5401 GCAATATGGA AGCATCACCA CTATCGATGT GCCTTGGAAT GTAGCCTATG AGAAAGTCCA
5461 TTTACTGAGC CTTGTGGACC TCATGCAGCA GGAGGGAGGC CCCAGCGAAA TTGGGGATGC
5521 TTTGAGCTTT GCCGTGCGAT ATGTCACCTC AGAAGTCCAT GGTGCCAGGC CCGGAGCCTC
5581 GAAAGCGGTG GTTATCCTAG TCACAGATGT CTCCGTGGAT TCAGTGGATG CTGCAGCCGA
5641 GGCCGCCAGA TCCAACCGAG TGACAGTGTT CCCCATTGGA ATCGGGGATC GGTACAGTGA
5701 GGCCCAGCTG AGCAGCTTGG CAGGCCCAAA GGCTGGCTCC AATATGGTAA GGCTCCAGCG
5761 AATTGAAGAC CTCCCCACCG TGGCCACCCT GGGAAATTCC TTCTTCCACA AGCTGTGCTC
5821 TGGGTTTGAT AGAGTTTGCG TGGATGAGGA TGGGAATGAG AAGAGGCCCG GGGATGTCTG
5881 GACCTTGCCA GACCAGTGCC ACACAGTGAC TTGCCTGCCA GATGGCCAGA CCTTGCTGAA
5941 GAGTCATCGG GTCAACTGTG ACCGGGGGCC AAGGCCTTCG TGCCCCAATG CCAGCCCCC
6001 TCTCAGGGTA GAGGAGACCT GTGGCTGCCG CTGGACCTGT CCCTGTGTGT GCATGGGCAG
6061 CTCTACCCGG CACATCGTGA CCTTTGATGG GCAGAATTTC AAGCTGACTG GCAGCTGTTC
6121 GTATGTCCTA TTTCAAAACA AGGAGCAGGA CCTGGAGGTG ATTCTCCAGA ATGGTGCCTG
6181 CAGCCCTGGG GCGAAGGAGA CCTGCATGAA ATCCATTGAG GTGAAGCATG ACGGCCTCTC
6241 AGTTGAGCTC CACAGTGACA TGCAGATGAC AGTGAATGGG AGACTAGTCT CCATCCCATA
6301 TGTGGGTGGA GACATGGAAG TCAATGTTTA TGGACCATC ATGTATGAGG TCAGATTCAA
6361 CCATCTTGGC CACATCTTCA CATTCACCCC CCAAAACAAT GAGTTCCAGC TGCAGCTCAG
```

FIGURE 1C

```
6421 CCCCAGGACC TTTGCTTCGA AGACATATGG TCTCTGTGGG ATCTGTGATG AGAACGGAGC
6481 CAATGACTTC ATTCTGAGGG ATGGGACAGT CACCACAGAC TGGAAGGCAC TCATCCAGGA
6541 ATGGACCGTA CAGCAGCTTG GGAAGACATC CCAGCCTGTC CATGAGGAGC AGTGTCCTGT
6601 CTCCGAATTC TTCCACTGCC AGGTCCTCCT CTCAGAATTG TTTGCCGAGT GCCACAAGGT
6661 CCTCGCTCCA GCCACCTTTT ATGCCATGTG CCAGCCCGAC AGTTGCCACC CGAAGAAAGT
6721 GTGTGAGGCG ATTGCCTTGT ATGCCCACCT CTGTCGGACC AAAGGGGTCT GTGTGGACTG
6781 GAGGAGGGCC AATTTCTGTG CTATGTCATG TCCACCATCC CTGGTGTACA ACCACTGTGA
6841 GCATGGCTGC CCTCGGCTCT GTGAAGGCAA TACAAGCTCC TGTGGGGACC AACCCTCGGA
6901 AGGCTGCTTC TGCCCCCCAA ACCAAGTCAT GCTGGAAGGT AGCTGTGTCC CCGAGGAGGC
6961 CTGTACCCAG TGCATCAGCG AGGATGGAGT CCGGCACCAG TTCCTGGAAA CCTGGGTCCC
7021 AGCCCACCAG CCTTGCCAGA TCTGCACGTG CCTCAGTGGG CGGAAGGTCA ACTGTACGTT
7081 GCAGCCCTGC CCCACAGCCA AGCTCCCAC CTGTGGCCCG TGTGAAGTGG CCCGCCTCCG
7141 CCAGAACGCA GTGCAGTGCT GCCCGGAGTA CGAGTGTGT TGTGACCTGG TGAGCTGTGA
7201 CCTGCCCCCG GTGCCTCCCT GCGAAGATGG CCTCCAGATG ACCCTGACCA ATCCTGGCGA
7261 GTGCAGACCC AACTTCACCT GTGCCTGCAG GAAGGATGAA TGCAGACGGG AGTCCCCGCC
7321 CTCTTGTCCC CCGCACCGGA CGCCGGCCCT TCGGAAGACT CAGTGCTGTG ATGAGTATGA
7381 GTGTGCATGC AACTGTGTCA ACTCCACGGT GAGCTGCCCG CTTGGGTACC TGGCCTCGGC
7441 TGTCACCAAC GACTGTGGCT GCACCACAAC AACCTGCTTC CCTGACAAGG TGTGTGTCCA
7501 CCGAGGCACC ATCTACCCTG TGGGCCAGTT CTGGGAGGAG GCCTGTGACG TGTGCACCTG
7561 CACGGACTTG GAGGACTCTG TGATGGGCCT GCGTGTGGCC CAGTGCTCCC AGAAGCCCTG
7621 TGAGGACAAC TGCCTGTCAG GCTTCACTTA TGTCCTTCAT GAAGGCGAGT GCTGTGGAAG
7681 GTGTCTGCCA TCTGCCTGTG AGGTGGTCAC TGGTTCACCA CGGGGCGACG CCCAGTCTCA
7741 CTGGAAGAAT GTTGGCTCTC ACTGGGCCTC CCCTGACAAC CCCTGCCTCA TCAATGAGTG
7801 TGTCCGAGTG AAGGAAGAGG TCTTTGTGCA ACAGAGGAAT GTCCTGCC CCCAGCTGAA
7861 TGTCCCCACC TGCCCCACGG GCTTCCAGCT GAGCTGTAAG ACCTCAGAGT GTTGTCCCAC
7921 CTGTCACTGC GAGCCCTGG AGGCCTGCTT GCTCAATGGT ACCATCATTG GGCCGGGGAA
7981 AAGTCTGATG ATTGATGTGT GTACAACCTG CCGCTGCACC GTGCCGGTGG GAGTCATCTC
8041 TGGATTCAAG CTGGAGGGCA GGAAGACCAC CTGTGAGGCA TGCCCCCTGG GTTATAAGGA
8101 AGAGAAGAAC CAAGGTGAAT GCTGTGGGAG ATGTCTGCCT ATAGCTTGCA CCATTCAGCT
8161 AAGAGGAGGA CAGATCATGA CACTGAAGCG TGATGAGACT ATCCAGGATG GCTGTGACAG
8221 TCACTTCTGC AAGGTCAATG AAAGAGGAGA GTACATCTGG GAGAAGAGAG TCACGGGTTG
8281 CCCACCTTTC GATGAACACA AGTGTCTGGC TGAGGGAGGA AAAATCATGA AAATTCCAGG
8341 CACCTGCTGT GACACATGTG AGGAGCCAGA ATGCAAGGAT ATCATTGCCA AGCTGCAGCG
8401 TGTCAAAGTG GGAGACTGTA AGTCTGAAGA GGAAGTGGAC ATTCATTACT GTGAGGGTAA
8461 ATGTGCCAGC AAAGCCGTGT ACTCCATCCA CATGGAGGAT GTGCAGGACC AGTGCTCCTG
8521 CTGCTCGCCC ACCCAGACGG AGCCCATGCA GGTGGCCCTG CGCTGCACCA ATGGCTCCCT
8581 CATCTACCAT GAGATCCTCA ATGCCATCGA ATGCAGGTGT CCCCCAGGA AGTGCAGCAA
8641 GTGAGGCCAC TGCCTGGATG CTACTGTCGC CTGCCTTACC CGACCTCACT GGACTGGCCA
8701 GAGTGCTGCT CAGTCCTCCT CAGTCCTCCT CCTGCTCTGC TCTTGTGCTT CCTGATCCCA
8761 CAATAAAGGT CAATCTTTCA CCTTGAAAAA AAAAAAAAA AA
```

```
Human   MIPARFAGVLLALALILPGTLCAEGTRGRSSTARCSLFGSDFVNTFDGSMYSFAGYCSYL    60
Dog     -S-T-LVR----------K--TK--V----M-----L-G--I----E-------D----
                                      *
Human   LAGGCQKRSFSIIGDFQNGKRVSLSVYLGEFFDIHLFVNGTVTQGDQRVSMPYASKGLYL   120
Dog     ---D--EH-I-L--G---D--------------------ML--T-SI------N----

Human   ETEAGYYKLSGEAYGFVARIDGSGNFQVLLSDRYFNKTCGLCGNFNIFAEDDFMTQEGTL   180
Dog     -A--------S----------N-----------------------------K------

Human   TSDPYDFANSWALSSGEQWCERASPPSSSCNISSGEMQKGLWEQCQLLKSTSVFARCHPL   240
Dog     ------------------R-K-V-----P--V--D-V-QV----------A--------

Human   VDPEPFVALCEKTLCECAGGLECACPALLEYARTCAQEGMVLYGWTDHSACSPVCPAGME   300
Dog     -----------R---T-VQ-M--P-AV------A---Q-I---------V-R-A------

Human   YRQCVSPCARTCQSLHINEMCQERCVDGCSCPEGQLLDEGLCVESTECPCVHSGKRYPPG   360
Dog     -KE-----T-------VK-V---Q--------------H--G-A--S---A-Q-----

Human   TSLSRDCNTCICRNSQWICSNEECPGECLVTGQSHFKSFDNRYFTFSGICQYLLARDCQD   420
Dog     A--LQ--H-------L----------------------------V-H----Q----

Human   HSFSIVIETVQCADDRDAVCTRSVTVRLPGLHNSLVKLKHGAGVAMDGQDVQLPLLKGDL   480
Dog     -T--V----------L-------------H--------N-G--S-----I-I---Q---

Human   RIQHTVTASVRLSYGEDLQMDWDGRGRLLVKLSPVYAGKTCGLCGNYNGNQGDDFLTPSG   540
Dog     ------M--------------S-V------T-Y-A-------RG------R----V--A-

Human   LAEPRVEDFGNAWKLHGDCQDLQKQHSDPCALNPRMTRFSEEACAVLTSPTFEACHRAVS   600
Dog     ----L----------L-A-EN-----R---S----QA--A-----L---SK--P-----G Human   PLPYLRNCRYDVCSCSDGRECLCGALASYAAACAGRGVRVAWREPGRCELNCPKGQVYLQ   660
Dog     -Q--VQ--L----------D---S-V-N----V-R---HI------F-A-S--Q-----

Human   CGTPCNLTCRSLSYPDEECNEACLEGCFCPPGLYMDERGDCVPKAQCPCYYDGEIFQPED   720
Dog     ------M--L------E-D---V---S--S-----L--------------------

Human   IFSDHHTMCYCEDGFMHCTMSGVPGSLLPDAVLSSPLSHRSKRSLSCRPPMVKLVCPADN   780
Dog     -------------------T--GL-----NP-----RC-----------------

Human   LRAEGLECTKTCQNYDLECMSMGCVSGCLCPPGMVRHENRCVALERCPCFHQGKEYAPGE   840
Dog     P-------A--------Q---T---------Q--------------------Q------

Human   TVKIGCNTCVCRDRKWNCTDHVCDATCSTIGMAHYLTFDGLKYLFPGECQYVLVQDYCGS   900
Dog     ----D-----------T----------A-------------------------

Human   NPGTFRILVGNKGCSHPSVKCKKRVTILVEGGEIELFDGEVNVKRPMKDETHFEVVESGR   960
Dog     ----L------E---Y----------------------K-------------Q Human   YIILLLGKALSVVWDRHLSISVVLKQTYQEKVCGLCGNFDGIQNNDLTSSNLQVEEDPVD  1020
Dog     -V-----------HR-----T--R----Q--------------F---S--I------

Human   FGNSWKVSSQCADTRKVPLDSSPATCHNNIMKQTMVDSSCRILTSDVFQDCNKLVDPEPY  1080
Dog     -------NP-----K----------V-----------------I-----R------F
```

FIGURE 2A

```
Human  LDVCIYDTCSCESIGDCACFCDTIAAYAHVCAQHGKVVTWRTATLCPQSCEERNLRENGY   1140
Dog    --I-----------T--------------------A-----F---N------H----

Human  ECEWRYNSCAPACQVTCQHPEPLACPVQCVEGCHAHCPPGKILDELLQTCVDPEDCPVCE   1200
Dog    -------------PI-------------------------------I-----------

Human  VAGRRFASGKKVTLNPSDPEHCQICHCDVVNLTCEACQEPGGLVVPPTDAPVSPTTLYVE   1260
Dog    -----L-P---II------------N--G--F--K--R---SV------G-IGS--S---

Human  DISEPPLHDFYCSRLLDLVFLLDGSSRLSEAEFEVLKAFVVDMMERLRISQKWVRVAVVE   1320
Dog    -T--------H----------------K---D----*--V---G---H-H----RI------

Human  YHDGSHAYIGLKDRKRPSELRRIASQVKYAGSQVASTSEVLKYTLFQIFSKIDRPEASRI   1380
Dog    ----------E--------------T---------E----------------G----------

Human  ALLLMASQEPQRMSRNFVRYVQGLKKKKVIVIPVGIGPHANLKQIRLIEKQAPENKAFVL   1440
Dog    -----------S-LA--L-----------------------S----H------------F Human  SSVDELEQQRDEIVSYLCDLAPEAPPPTLPPHMAQVTVGPGLLGVSTLGPKRNSMVLDVA   1500
Dog    -G------R----IN----------A--QH-P-------SE-----SP----------V Human  FVLEGSDKIGEADFNRSKEFMEEVIQRMDVGQDSIHVTVLQYSYMVTVEYPFSEAQSKGD   1560
Dog    ------------N--K-R--------------R----------------T--------E Human  ILQRVREIRYQGGNRTNTGLALRYLSDHSFLVSQGDREQAPNLVYMVTGNPASDEIKRLP   1620
Dog    V--Q--D---R----------Q---E---S--------V------------------M-

Human  GDIQVVPIGVGPNANVQELERIGWPNAPILIQDFETLPREAPDLVLQRCCSGEGLQIPTL   1680
Dog    ------------H-------K---------H---M------------------------

Human  SPAPDCSQPLDVILLLDGSSSFPASYFDEMKSFAKAFISKANIGPRLTQVSVLQYGSITT   1740
Dog    --T---------V---------I------------T-----R--------------

Human  IDVPWNVVPEKAHLLSLVDVMQREGGPSQIGDALGFAVRYLTSEMHGARPGASKAVVILV   1800
Dog    --------AY--V--------L--Q-----E-----S-----V---V------------

Human  TDVSVDSVDAAADAARSNRVTVFPIGIGDRYDAAQLRILAGPAGDSNVVKLQRIEDLPTM   1860
Dog    -------------E-----------------SE---SS----KAG--M-R---------V Human  VTLGNSFLHKLCSGFVRICMDEDGNEKRPGDVWTLPDQCHTVTCQPDGQTLLKTHRVNCD   1920
Dog    A------F-------D-V-V-------------------------L--------S------

Human  RGLRPSCPNSQSPVKVEETCGCRWTCPCVCTGSSTRHIVTFDGQNFKLTGSCSYVLFQNK   1980
Dog    --P------G-P-LR-------------M-------------------------------

Human  EQDLEVILHNGACSPGARQGCMKSIEVKHSALSVELHSDMEVTVNGRLVSVPYVGGNMEV   2040
Dog    --------Q----------KET--------DG---------QM--------I-----D---

Human  NVYGAIMHEVRFNHLGHIFTFTPQNNEFQLQLSPKTFASKTYGLCGICDENGANDFMLRD   2100
Dog    ----T--Y--------------------R---------------------I---

Human  GTVTTDWKTLVQEWTVQRPGQTCQPILEEQCLVPDSSHCQVLLLPLFAECHKVLAPATFY   2160
Dog    --------A-I------QL-K-S--VH----P-SEFF------SE-------------
```

FIGURE 2B

```
Human   AICQQDSCHQEQVCEVIASYAHLCRTNGVCVDWRTPDFCAMSCPPSLVYNHCEHGCPRHC    2220
Dog     -M--P----PKK---A--L-------K-------RAN--------------------L-

Human   DGNVSSCGDHPSEGCFCPPDKVMLEGSCVPEEACTQCIGEDGVQHQFLEAWVPDHQPCQI    2280
Dog     E--T-----Q---------NQ-----------------S----R-----T---A------

Human   CTCLSGRKVNCTTQPCPTAKAPTCGLCEVARLRQNADQCCPEYECVCDPVSCDLPPVPHC    2340
Dog     -------------L------------P----------V-----------L---------P-

Human   ERGLQPTLTNPGECRPNFTCACRKEECKRVSPPSCPPHRLPTLRKTQCCDEYECACNCVN    2400
Dog     -D---M-----------------D--R-E---------T-A------------------

Human   STVSCPLGYLASTATNDCGCTTTTCLPDKVCVHRSTIYPVGQFWEEGCDVCTCTDMEDAV    2460
Dog     -------------AV-----------F--------G-----------A--------L--S-

Human   MGLRVAQCSQKPCEDSCRSGFTYVLHEGECCGRCLPSACEVVTGSRGLSQSSWKSVGSQ     2520
Dog     ---------------N-L--------------------------|---|A--H--N---H Human   WASPENPCLINECVRVKEEVFIQQRNVSCPQLEVPVCPSGFQLSCKTSACCPSCRCERME    2580
Dog     ----D---------------V----------N--T--T---------E---T-H--PL- Human   ACMLNGTVIGPGKTVMIDVCTTCRCMVQVGVISGFKLECRKTTCNPCPLGYKEENNTGEC    2640
Dog     --L----I-----SL----------T-P----------G-----EA--------K-Q---

Human   CGRCLPTACTIQLRGGQIMTLKRDETLQDGCDTHFCKVNERGEYFWEKRVTGCPPFDEHK    2700
Dog     ------I----------------I-----S-----------I----------------

Human   CLAEGGKIMKIPGTCCDTCEEPECNDITARLQYVKVGSCKSEVEVDIHYCQGKCASKAMY    2760
Dog     -----------------------K--I-K--R----D----E-------E-------V-

Human   SIDINDVQDQCSCCSPTRTEPMQVALHCTNGSVVYHEVLNAMECKCSPRKCSK           2813
Dog     --HME----------Q--------R-----LI---I---I--R--------
```

FIGURE 2C

```
exon 4      AAATGACAAAAGAGTGAGCCGGTC*
AGGGGGTTTCCAAAATGACAAAAGAGTGAGCCTCTCCGTGTATCTCGGAGAATTTTTCGA
   G  G  F  Q  N  D  K  R  V  S  L  S  V  Y  L  G  E  F  F  D CATTCATTTGTTTGTCAATGGTACCATGCTGCAGGGGACCCAAAGGTAAGTCAGAAGCCC
   I  H  L  F  V  N  G  T  M  L  Q  G  T  Q  R

GAATGTTCAGGTTAATATGGACCCTGGGGATCACTTTGCAACCCCCTTGTTTTTTCAGAT

GAGGGAGCCGGGGCCCAGAGACAGGAAGTAAATGTGCCCAGGGAAAGTGAGTGGCAGGAC

TGGGTGAAAGCCCCATATCCCGACTCCTGGTCAAGGAGACTTTGCACCAAGGTCCCAGCC
              3'-GGGCTGGCGACCAGTTCCTCTGAA-5'

CTGGAGCATGGGGTTGGGGTTGGAAGGTGGAGGGACATGGAGGAAATGCATGAGAAGCAC
                              exon 5
GCTTCCTGAGCTCCTCCTTGTCCCACCAGCATCTCCATGCCCTACGCCTCCAATGGGC
                                I  S  M  P  Y  A  S  N  G
```

FIGURE 4

DNA ENCODING CANINE VON WILLEBRAND FACTOR AND METHODS OF USE

This application is a continuation of Ser. No. 08/896,449, filed Jul. 18, 1997, now U.S. Pat. No. 6,040,143.

FIELD OF THE INVENTION

This invention relates generally to canine von willebrand factor (vWF), and more particularly, to the gene encoding vWF as well as a genetic defect that causes canine von Willebrand's disease.

BIOLOGICAL DEPOSITS

| SEQUENCE | ACCESSION NO. |
|---|---|
| Canine von Willebrand Factor | AF 099154 |

BACKGROUND OF THE INVENTION

In both dogs and humans, von Willebrand's disease (vWD) is a bleeding disorder of variable severity that results from a quantitative or qualitative defect in von Willebrand factor (vWF) (Ginsburg, D. et al., *Blood* 79:2507–2519 (1992); Ruggeri, Z. M., et al., *FASEB J* 7:308–316 (1993); Dodds, W. J., *Mod Vet Pract* 681–686 (1984); Johnson, G. S. et al., *JAVMA* 176:1261–1263 (1988); Brooks, M., *Probl In Vet Med* 4:636–646 (1992)). This clotting factor has two known functions, stabilization of Factor VIII (hemophilic factor A) in the blood, and aiding the adhesion of platelets to the subendothelium, which allows them to provide hemostasis more effectively. If the factor is missing or defective, the patient, whether human or dog, may bleed severely.

The disease is the most common hereditary bleeding disorder in both species, and is genetically and clinically heterogenous. Three clinical types, called 1, 2, and 3 (formerly I, II, and III; see Sadler, J. E. et al., *Blood* 84:676–679 (1994) for nomenclature changes), have been described. Type 1 vWD is inherited in a dominant, incompletely penetrant fashion. Bleeding appears to be due to the reduced level of vWF rather than a qualitative difference. Although this is the most common form of vWD found in most mammals, and can cause serious bleeding problems, it is generally less severe than the other two types. In addition, a relatively inexpensive vasopressin analog (DDAVP) can help alleviate symptoms (Kraus, K. H. et al., *Vet Surg* 18:103–109 (1989)).

In Type 2 vWD, patients have essentially normal levels of vWF, but the factor is abnormal as determined by specialized tests (Ruggeri, Z. M., et al., *FASEB J* 7:308–316 (1993); Brooks, M., *Probl In Vet Med* 4:636–646 (1992)). This type is also inherited in a dominant fashion and has only rarely been described in dogs (Turrentine, M. A., et al., *Vet Clin North Am Small Anim Pract* 18:275 (1988)).

Type 3 vWD is the most severe form of the disease. It is inherited as an autosomal recessive trait, and affected individuals have no detectable vWF in their blood. Serious bleeding episodes require transfusions of blood or cryoprecipitate to supply the missing vWF. Heterozygous carriers have moderately reduced factor concentrations, but generally appear to have normal hemostasis.

Scottish terriers have Type 3 vWD (Dodds, W. J., *Mod Vet Pract* 681–686 (1984); Johnson, G. S. et al., *JAVMA* 176:1261–1263 (1988)). Homozygotes have no detectable vWF and have a severe bleeding disorder. Heterozygotes have reduced levels of the factor, and are clinically normal (Brooks, M. et al., *JAVMA* 200:1123–1127 (1992)). The prevalence of vWD among Scottish terriers including both heterozygotes and homozygotes has been variously estimated from 27–31% (Stokol, T. et al., *Res. Vet. Sci.* 59:152–155 (1995); Brooks, M., *Proc. 9th ACVIM Forum* 89–91 (1991)).

Currently, detection of affected and carrier Scottish terrier dogs is done by vWF antigen testing (Benson, R. E. et al., *Am J Vet Res* 44:399–403 (1983); Stokol, T. et al., *Res. Vet. Sci.* 59:152–155 (1995)) or by coagulation assays (Rosborough, T. K. et al., *J. Lab. Clin. Med.* 96:47–56 (1980); Read, M. S. et al., *J. Lab. Clin. Med.* 101:74–82 (1983)). These procedures yield variable results, as the protein-based tests can be influenced by such things as sample collection, sample handling, estrous, pregnancy, vaccination, age, and hypothyroidism (Strauss, H. S. et al., *New Eng J Med* 269:1251–1252 (1963); Bloom, A. L., *Mayo Clin Proc* 66:743–751 (1991); Stirling, Y. et al., *Thromb Haemostasis* 52:176–182 (1984); Mansell, P. D. et al., *Br. Vet. J.* 148:329–337 (1992); Avgeris, S. et al., *JAVMA* 196:921–924 (1990); Panciera, D. P. et al., *JAVMA* 205:1550–1553 (1994)). Thus, for example, a dog that tests within the normal range on one day, can test within the carrier range on another day. It is therefore difficult for breeders to use this information.

It would thus be desirable to provide the nucleic acid sequence encoding canine vWF. It would also be desirable to provide the genetic defect responsible for canine vWD. It would further be desirable to obtain the amino acid sequence of canine vWF. It would also be desirable to provide a method for detecting carriers of the defective vWF gene based on the nucleic acid sequence of the normal and defective vWF gene.

SUMMARY OF THE INVENTION

The present invention provides a novel purified and isolated nucleic acid sequence encoding canine vWF. A nucleic acid sequence containing the mutation that causes vWD in Scottish terriers, a single-base deletion in exon 4, is also provided. The nucleic acid sequences of the present invention may be used in methods for detecting carriers of the mutation that causes vWD. Such methods may be used by breeders to reduce the frequency of the disease-causing allele and the incidence of disease. In addition, the nucleic acid sequence of the canine vWF provided herein may be used to determine the genetic defect that causes vWD in other breeds as well as other species.

Additional objects, advantages, and features of the present invention will become apparent from the following description, taken in conjunction with the accompanying drawings.

BRIEF DESCRIPTION OF THE DRAWINGS

The various advantages of the present invention will become apparent to one skilled in the art by reading the following specification and by referencing the following drawings in which:

FIGS. 1A–1C is the nucleic acid sequence of the canine von Willebrand factor of the present invention;

FIGS. 2A–2C is a comparison of the human and canine prepro-von Willebrand factor amino acid sequences;

FIG. 4 illustrates the results of a method of the present invention used to detect the Scottish terrier vWD mutation.

DETAILED DESCRIPTION OF THE PREFERRED EMBODIMENTS

Figure 3:
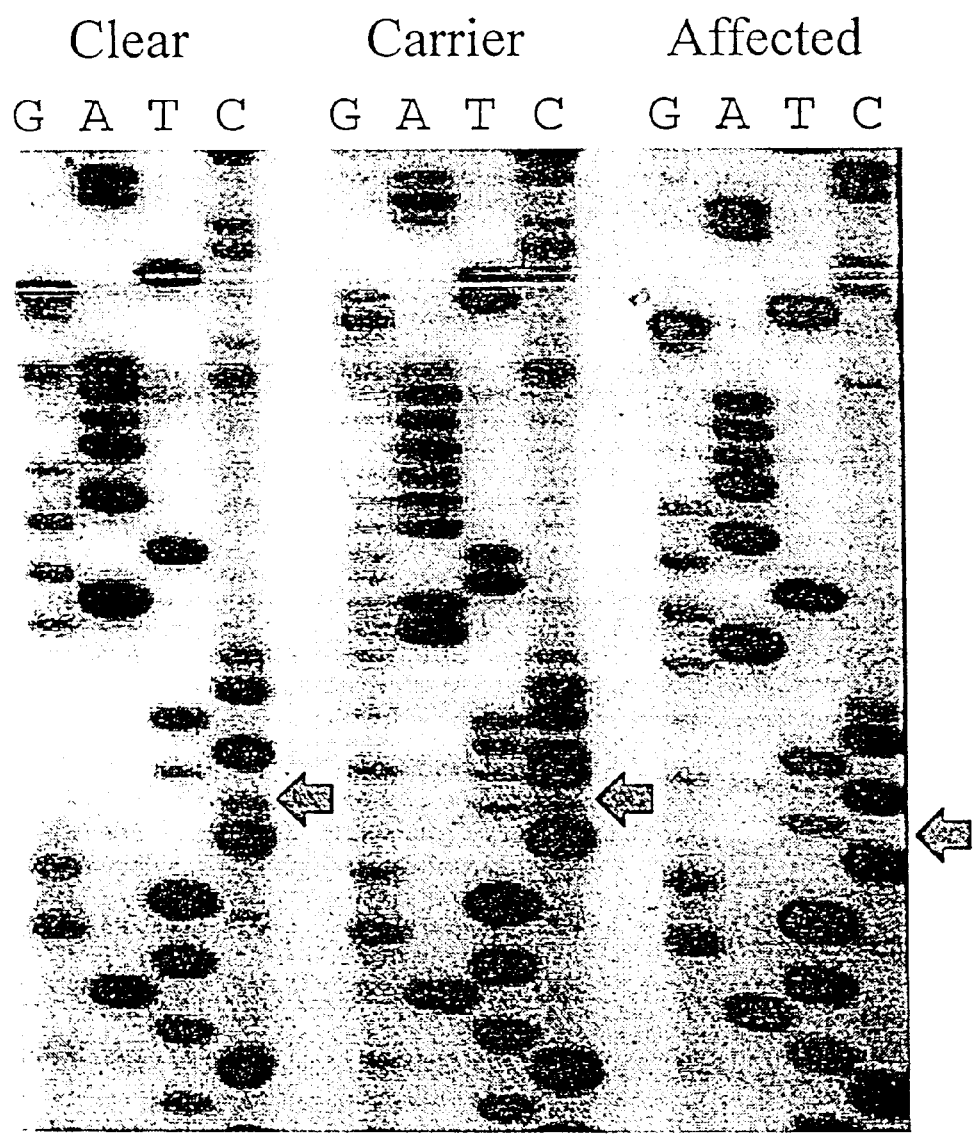
FIG. 3 provides nucleotide sequencing ladders for the von Wilebrand's disease mutation region for normal (clear), carrier, and affected Scottish terriers, the sequences being obtained directly from PCR products derived from genomic DNAs in exon 4.

The cDNA encoding canine von Willebrand Factor (vWF) has been sequenced, and its sequence is set forth in FIGS. 1A–1C and SEQ ID NO: 1. The amino acid sequence corresponding to the cDNA of canine vWF has been subsequently deduced and is set forth in FIGS. 2A–2C and SEQ ID NO: 2. The mutation of the normal vWF gene which causes von Willebrand's Disease (vWD), a deletion at codon 88 of the normal gene resulting in a frameshift, is also provided. The nucleic acid sequences of the present invention may be used in methods for detecting homozygous and heterozygous carriers of the defective vWF gene.

In a preferred method of detecting the presence of the von Willebrand allele in canines, DNA samples are first collected by relatively noninvasive techniques, i.e., DNA samples are obtained with minimal penetration into body tissues of the animals to be tested. Common noninvasive tissue sample collection methods may be used and include withdrawing buccal cells via cheek swabs and withdrawing blood samples. Following isolation of the DNA by standard techniques, PCR is performed on the DNA utilizing pre-designed primers that produce enzyme restriction sites on those DNA samples that harbor the defective gene. Treatment of the amplified DNA with appropriate restriction enzymes such as BsiE I thus allows one to analyze for the presence of the defective allele. One skilled in the art will appreciate that this method may be applied not only to Scottish terriers, but to other breeds such as Shetland sheep-dogs and Dutch Kooikers.

Overall, the present invention provides breeders with an accurate, definitive test whereby the undesired vWD gene may be eliminated from breeding lines. The current tests used by breeders are protein-based, and as noted previously, the primary difficulty with this type of test is the variability of results due to a variety of factors. The ultimate result of such variability is that an inordinate number of animals fall into an ambiguous grouping whereby carriers and noncarriers cannot be reliably distinguished. The present invention obviates the inherent limitations of protein-based tests by detecting the genetic mutation which causes vWD. As described in Specific Example 1, the methods of the present invention provide an accurate test for distinguishing noncarriers, homozygous carriers and heterozygous carriers of the defective vWF gene.

It will be appreciated that because the vWF cDNA of the present invention is substantially homologous to vWF cDNA throughout the canine species, the nucleic acid sequences of the present invention may be used to detect DNA mutations in other breeds as well. In addition, the canine vWF sequence presented herein potentially in combination with the established human sequence (Genbank Accession No. X04385, Bonthron, D. et al., *Nucleic Acids Res.* 14:7125–7128 (1986); Mancuso, D. J. et al., *Biochemistry* 30:253–269 (1989); Meyer, D. et al., *Throm Haemostasis* 70:99–104 (1993)), may be used to facilitate sequencing of the vWF gene and genetic defects causing vWD, in other mammalian species e.g., by using cross-species PCR methods known by those skilled in the art.

It is also within the contemplation of this invention that the isolated and purified nucleic acid sequences of the present invention be incorporated into an appropriate recombinant expression vector, e.g., viral or plasmid, which is capable of transforming an appropriate host cell, either eukaryotic (e.g., mammalian) or prokaryotic (e.g., *E. coli*). Such DNA may involve alternate nucleic acid forms, such as cDNA, gDNA, and DNA prepared by partial or total chemical synthesis. The DNA may also be accompanied by additional regulatory elements, such as promoters, operators and regulators, which are necessary and/or may enhance the expression of the vWF gene product. In this way, cells may be induced to over-express the vWF gene, thereby generating desired amounts of the target vWF protein. It is further contemplated that the canine vWF polypeptide sequence of the present invention may be utilized to manufacture canine vWF using standard synthetic methods. One skilled in the art will also note that the defective protein encoded by the defective vWF gene of the present invention may also be of use in formulating a complementary diagnostic test for canine vWD that may provide further data in establishing the presence of the defective allele. Thus, production of the defective vWF polypeptide, either through expression in transformed host cells as described above for the active vWF polypeptide or through chemical synthesis, is also contemplated by the present invention.

The term "gene" as to referred herein means a nucleic acid which encodes a protein product. The term "nucleic acid" refers to a linear array of nucleotides and nucleosides, such as genomic DNA, cDNA and DNA prepared by partial or total chemical synthesis from nucleotides. The term "encoding" means that the nucleic acid may be transcribed and translated into the desired polypeptide. "Polypeptide" refers to amino acid sequences which comprise both full-length proteins and fragments thereof. "Mutation" as referred to herein includes any alteration in a nucleic acid sequence including, but not limited to, deletions, substitutions and additions.

As referred to herein, the term "capable of hybridizing under high stringency conditions" means annealing a strand of DNA complementary to the DNA of interest under highly stringent conditions. Likewise, "capable of hybridizing under low stringency conditions" refers to annealing a strand of DNA complementary to the DNA of interest under low stringency conditions. In the present invention, hybridizing under either high or low stringency conditions would involve hybridizing a nucleic acid sequence (e.g., the complementary sequence to SEQ ID NO: 1 or portion thereof), with a second target nucleic acid sequence. "High stringency conditions" for the annealing process may involve, for example, high temperature and/or low salt content, which disfavor hydrogen bonding contacts among mismatched base pairs. "Low stringency conditions" would involve lower temperature, and/or lower salt concentration than that of high stringency conditions. Such conditions allow for two DNA strands to anneal if substantial, though not near complete complementarity exists between the two strands, as is the case among DNA strands that code for the same protein but differ in sequence due to the degeneracy of the genetic code. Appropriate stringency conditions which promote DNA hybridization, for example, 6×SSC at about 45° C., followed by a wash of 2×SSC at 50° C. are known to those skilled in the art or can be found in *Current Protocols in Molecular Biology*, John Wiley & Sons, NY (1989), 6.31–6.3.6. For example, the salt concentration in the wash step can be selected from a low stringency of about 2×SSC at 50° C. to a high stringency of about 0.2×SSC at 50° C. In addition, the temperature in the wash step can be increased from low stringency at room temperature, about 22° C., to high stringency conditions, at about 65° C. Other stringency parameters are described in Maniatis, T., et al., *Molecular Cloning: A Laboratory Manual, Cold Spring Harbor Laboratory Press*, Cold Spring N.Y., (1982), at pp. 387–389; see also Sambrook J. et al., *Molecular Cloning: A Laboratory Manual*, Second Edition, Volume 2, Cold Spring Harbor Laboratory Press, Cold Spring, N.Y. at pp. 8.46–8.47 (1989).

SPECIFIC EXAMPLE 1

Materials And Methods

Isolation of RNA. The source of the RNA was a uterus from a Scottish Terrier affected with vWD (factor level <0.1% and a clinical bleeder), that was surgically removed because of infection. Spleen tissue was obtained from a Doberman Pinscher affected with vWD that died from dilated cardiomyopathy (factor level 7% and a clinical bleeder). Total RNA was extracted from the tissues using Trizol (Life Technologies, Gaithersburg, Md.). The integrity of the RNA was assessed by agarose gel electrophoresis.

Design of PCR primer sets. Primers were designed to a few regions of the gene, where sequences from two species were available (Lavergne, J. M. et al., *Biochem Biophys Res Commun* 194:1019–1024 (1993); Bakhshi, M. R. et al., *Biochem Biophys Acta* 1132:325–328 (1992)). These primers were designed using rules for cross-species' amplifications (Venta et al., "Genes-Specific Universal Mammalian Sequence-Tagged Sites: Application To The Canine Genome" *Biochem. Genet.* (1996) in press). Most of the primers had to be designed to other regions of the gene using the human sequence alone (Mancuso, D. J. et al., *Biochemistry* 30:253–269 (1991)). Good amplification conditions were determined by using human and canine genomic DNAs.

Reverse Transcriptase-PCR. Total RNA was reverse transcribed using random primers (Bergenhem, N. C. H. et al., *PNAS* (USA) 89:8789–8802 (1992)). The cDNA was amplified using the primer sets shown to work on canine genomic DNA.

DNA Sequence Analysis. Amplification products of the predicted sizes were isolated from agarose gels by adsorption onto silica gel particles using the manufacturer's method (Qiagen, Chatsworth, Calif.). Sequences were determined using $^{32}$P-5' end-labeled primers and a cycle sequencing kit (United States Biochemical Corp., Cleveland, Ohio). The sequences of the 5' and 3' untranslated regions were determined after amplification using Marathon™ RACE kits (Clontech, Palo Alto, Calif.). Sequences were aligned using the Eugene software analysis package (Lark Technologies, Houston, Tex.). The sequence of the canine intron four was determined from PCR-amplified genomic DNA.

Design of a Diagnostic Test. PCR mutagenesis was used to create diagnostic and control BsiE I and Sau96 I restriction enzyme sites for the test. Amplification conditions for the test are: 94° C., 1 min, 61° C., 1 min, and 72° C., 1 min, for 50 cycles using cheek swab DNA (Richards, B. et al., *Human Molecular Genetics* 2:159–163 (1992)).

Population Survey. DNA was collected from 87 Scottish terriers from 16 pedigrees. DNA was isolated either from blood using standard procedures (Sambrook, J. et al., Cold Harbor Spring Lab, Cold Harbor Spring N.Y., 2nd Edition, (1989)) or by cheek swab samples (Richards, B. et al., *Human Molecular Genetics* 2:159–163 (1992)). The genetic status of each animal in the survey was determined using the BsiE I test described above.

Results

Comparison of the canine and human sequences. The alignment of the canine and human prepro-von Willebrand Factor amino acid sequences is shown in FIGS. 2A–2C. The location of the Scottish terrier vWD mutation is indicated by the "*". Potential N-glycosylation sites are shown in bold type. The known and postulated integrin binding sites are boxed. Amino acid numbers are shown on the right side of the figure. The human sequence is derived from Genbank accession number X04385 (Bonthron, D. et al., *Nucleic Acids Res.* 14:7125–7128 (1986)).

Overall, 85.1% sequence identity is seen between the prepro-vWF sequences. The pro-region is slightly less conserved than the mature protein (81.4% vs. 87.5%). There were no other noteworthy percentage sequence identity differences seen in other regions of the gene, or between the known repeats contained within the gene (data not shown). Fourteen potential N-linked glycosylation sites are present in the canine sequence, all of which correspond to similar sites contained within the human sequence. The two integrin binding sites identified in the human vWF protein sequence (Lankhof, H. et al., *Blood* 86:1035–1042 (1995)) are conserved in the canine sequence as well (FIGS. 2A–2C). The 5' and 3' untranslated regions have diverged to a greater extent than the coding region (data not shown), comparable to that found between the human and bovine sequences derived for the 5' flanking region (Janel, N. et al., *Gene* 167:291–295 (1995)). Additional insights into the structure and function of the von Willebrand factor can be gained by comparison of the complete human sequence (Mancuso, D. J. et al., *Biochemistry* 30:253–269 (1989); Meyer, D. et al., *Throm Haemostasis* 70:99–104 (1993)) and the complete canine sequence reported here.

The sequence for most of exon 28 was determined (Mancuso, D. J. et al., *Thromb Haemost* 69:980 (1993); Porter, C. A. et al., *Mol Phylogenet Evol* 5:89–101 (1996)). All three sequences are in complete agreement, although two silent variants have been found in other breeds (Table 1, exon 28). Partial sequences of exons 40 and 41 (cDNA nucleotide numbers 6923 to 7155, from the initiation codon) were also determined as part of the development of a polymorphic simple tandem repeat genetic marker (Shibuya, H. et al., *Anim Genet* 24:122 (1994)). There is a single nucleotide sequence difference between this sequence ("T") and the sequence of the present invention, ("C") at nucleotide position 6928.

Scottish Terrier vWD mutation. FIG. 3 shows nucleotide sequencing ladders for the von Willebrand's Disease mutation region for normal (clear), carrier, and affected Scottish terriers. The sequences were obtained directly from PCR products derived from genomic DNAs in exon 4. The arrowheads show the location of the C nucleotide that is deleted in the disease-causing allele. Note that in the carrier ladder each base above the point of the mutation has a doublet appearance, as predicted for deletion mutations. The factor levels reported for these animals were: Normal, 54%; Carrier, 34%; Affected, <0.1%.

As a result of the deletion, a frameshift mutation at codon 88 leads to a new stop codon 103 bases downstream. The resulting severely truncated protein of 119 amino acids does not include any of the mature von Willebrand factor region. The identity of the base in the normal allele was determined from an unaffected dog.

Development of a diagnostic test. A PCR primer was designed to produce a BsiE I site in the mutant allele but not in the normal allele (FIG. 4). The position of the deleted nucleotide is indicated by an asterisk. The altered nucleotides in each primer are underlined. The normal and mutant allele can also be distinguished using Sau96 I. The naturally occurring Sau96 I sites are shown by double underlines. The highly conserved donor and acceptor dinucleotide splice sequences are shown in bold type.

In order to ensure that the restriction enzyme cut the amplified DNA to completion, an internal control restriction site common to both alleles was designed into the non-diagnostic primer. The test was verified by digestion of the DNA from animals that were affected, obligate carriers, or normal (based on high factor levels [greater than 100% of normal] obtained from commonly used testing labs and reported to us by the owners, and also using breeds in which Type 3 vWD has not been observed). The expected results were obtained (e.g., FIG. 5). Five vWD-affected animals from a colony founded from Scottish terriers (Brinkhous, K. M. et al., *Ann. New York Acad. Sci.* 370:191–203 (1981)) were also shown to be homozygous for this mutation. An additional unaffected animal from this same colony was found to be clear.

It would still be possible to misinterpret the results of the test if restriction enzyme digestion was not complete, and if the rates of cleavage of the cont778rol and diagnostic sites were vastly different. The rates of cleavage of the two BsiE I sites were thus examined by partially digesting the PCR products and running them on capillary electrophoresis. The rates were found to be very nearly equal (the diagnostic site is cut 12% faster than the control site).

The mutagenesis primer was also designed to produce a Sau96 I site into the normal allele but not the mutant allele. This is the reverse relationship compared to the BsiE I-dependent test, with respect to which allele is cut. Natural internal Sau96 I sites serve as digestion control sites (shown in FIG. 4). The test using this enzyme produced identical genotypic results compared to the BsiE I for all animals examined (data not shown).

A possible mutation in the Doberman Pinscher gene. The complete Scottish terrier sequence was compared to the complete Doberman Pinscher sequence. Several nucleotide differences were found and were compared to the nucleotides found in the same position in the human sequence as shown in Table 1 below. Most of these changes were silent. However, of three amino acid changes, one is relatively non-conservative (F905L) and is proposed to be the mutation that causes Doberman Pinscher vWD. Other data strongly suggest that the nucleotide interchange at the end of exon 43 causes a cryptic splice site to be activated reducing the amount of normally processed mRNA, with a concomitant decrease in the amount of vWF produced.

Figure 5:
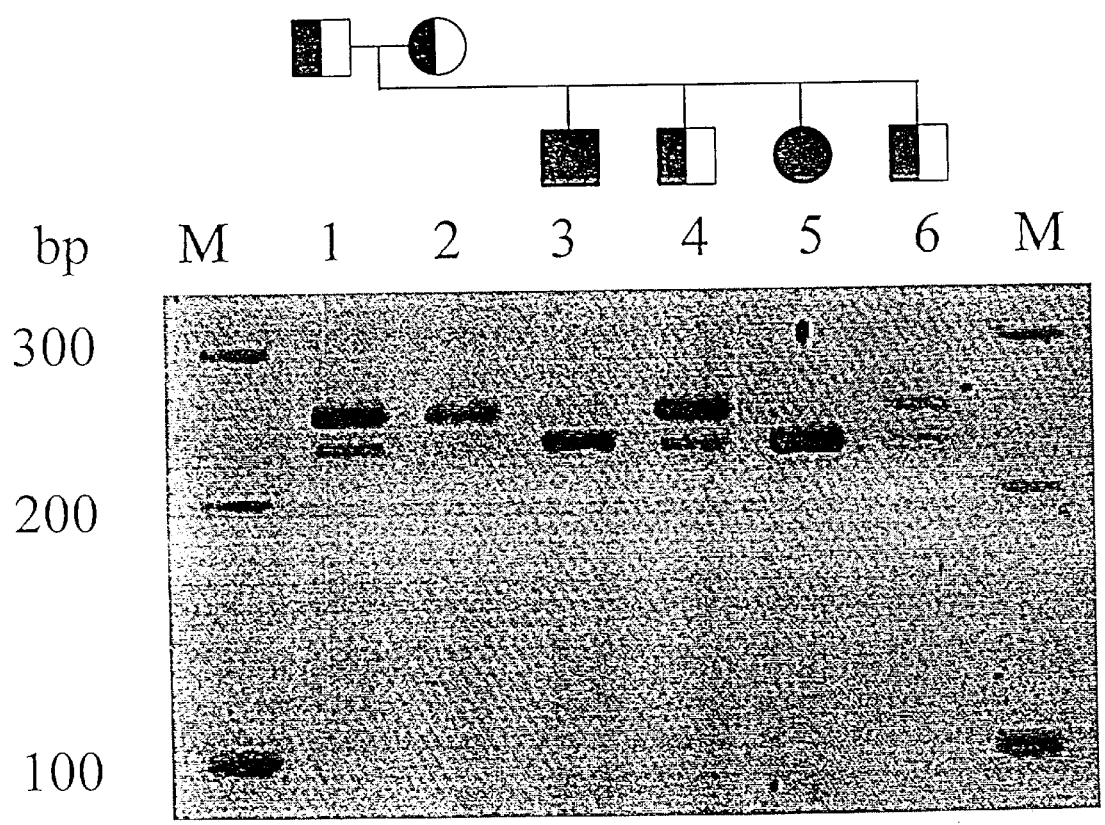
FIG. 5 shows the Scottish terrier pedigree, which in turn illustrates segregation of the mutant and normal vWF alleles.

Mendelian inheritance. One test often used to verify the correct identification of a mutant allele is its inheritance according to Mendel's law of segregation. Three pedigrees were examined in which the normal and mutant alleles were segregating, as shown in FIG. 5. Exon four of the vWF gene was PCR-amplified from genomic DNA. The PCR products were examined for the presence of the normal and mutant vWF alleles by agarose gel electrophoresis after digestion with BsiE I (see FIG. 5). The affected animals are homozygous for the mutant allele (229 bp; lanes 3 and 5). The other animals in this pedigree are heterozygotes (251 bp and 229 bp; lanes 1, 2, 4, and 6), including the obligate carrier parents.

TABLE 1

Differences Between Scottie And Doberman
Protein And Nucleotide von Willebrand Factor Sequences
With Comparison To The Human Sequences

| Exon | A.A.[1] | Amino Acid | | | Codon | | |
|---|---|---|---|---|---|---|---|
| | | Human | Scottie | Doberman | Human | Scottie | Doberman |
| 5' UT[2] | nuc-35[3] | N/A[4] | N/A | N/A | N/A | A | G |
| 4 | 85 | S | S/F.Shift[5] | S | TCC | TTC/TC_ | TCC |
| 5 | 173 | M | R | K | ATG | AGG | AAG |
| 11 | 422 | S | T | T | TCC | ACA | ACC |
| 21 | 898 | C | C | C | TGC | TGT | TGC |
| 21 | 905 | F | F | L | TTT | TTC | TTA |
| 24 | 1041 | S | S | S | TCA | TCA | TCG |
| 24 | 1042 | S | S | S | TCC | TCC | TCA |
| 28 | 1333 | D | D | E | GAC | GAC | GAG |
| 28 | 1349 | Y | Y | Y | TAT | TAT | TAC* |
| 42 | 2381 | P | L | P | CCC | CTG | CCG |
| 43 | 2479 | S | S | S | TCG | TCG | TCA |
| 45 | 2555 | P | P | P | CCC | CCC | CCG |
| 47 | 2591 | P | P | P | CCC | CCT | CCC |
| 49 | 2672 | D | D | D | GAT | GAT | GAC |
| 51 | 2744 | E | E | E | GAG | GAG | GAA |

[1]Amino acid residue position
[2]Untranslated region
[3]Nucleotide position
[4]Not Applicable
[5]Frameshift mutation
Boxed residues show amino acid differences between breeds
*This site has been shown to be polymorphic in some breeds
The mature VWF protein begins in exon 18

The alleles, as typed by both the BsiE I and Sau96 I tests, showed no inconsistencies with Mendelian inheritance. One of these pedigrees included two affected animals, two phenotypically normal siblings, and the obligate carrier parents. The two parents were found to be heterozygous by the test, the two affected animals were found to be homozygous for the mutant allele, and the normal siblings were found to be heterozygotes.

Population survey for the mutation. Cheek swabs or blood samples were collected from 87 animals in order to determine the incidence of carriers in the U.S. Scottish terrier population. Although we attempted to make the sample as random as possible, these dogs were found to come from 16 pedigrees, several of which are more distantly interconnected. This is due to some ascertainment bias, based on ownership (as opposed to phenotypic ascertainment bias). In these 87 animals four affected and 15 carrier animals were found.

Discussion

These results establish that the single base deletion found in exon four of the vWF gene causes vWD in the Scottish terrier breed. The protein produced from the mutant allele is extremely short and does not include any of the mature vWF protein. Four Scottish terriers known to be affected with the disease are homozygous for the mutation. Five other mixed-breed dogs descended from Scottish terriers, and affected with vWD, are also homozygous for the mutation. No normal animals are homozygous for the mutation. Unaffected obligate carriers are always heterozygous for the mutation.

The gene frequency, as determined from the population survey, appears to be around 0.13 resulting in a heterozygote frequency of about 23% and expected frequency of affected animals of about 2%. Although the sample size is relatively small and somewhat biased, these data are in general agreement with the protein-based surveys (Stokol, T. et al., Res Vet Sci 59:152–155 (1995); Brooks, M., Probl In Vet Med 4:636–646 (1992)), in that the allele frequency is substantial.

All data collected thus far indicate that this mutation accounts for essentially all of the von Willebrand's disease found in Scottish terriers. This result is consistent with the results found for other genetic diseases, defined at the molecular level, in various domestic animals (Shuster, D. E.

et al., *PNAS (USA)* 89:9225–9229 (1992); Rudolph, J. A. et al., *Nat Genet* 2:144–147 (1992); O'Brien, P. J. et al., *JAVMA* 203:842–851 (1993)). A likely explanation may be found in the pronounced founder effect that occurs in domestic animals, compared to most human and wild animal populations.

Published data using the protein-based factor assays have shown that, at least in several instances, obligate carriers have had factor levels that would lead to a diagnosis of "clear" of the disease allele. For example, in one study an obligate carrier had a factor level of 78% (Johnson, G. S. et al., *JAVMA* 176:1261–1263 (1980)). In another study, at least some of the obligate carriers had factor levels of 65% or greater (Brinkhous, K. M. et al., *Ann. New York Acad. Sci.* 370:191–203 (1981)). In addition, the number of animals that fall into an equivocal range can be substantial. In one study, 19% of Scottish terriers fell in this range (50–65% of the normal vWF antigen level) (Stokol, T. et al., *Res Vet Sci* 59:152–155 (1995)). Thus, although the protein-based tests have been useful, the certainty of the DNA-based test described herein should relieve the necessity of repeated testing and the variability associated with the protein-based assays.

The mutation is present in the pre-vWF part of the molecule. This part of the molecule is processed off prior to delivery of the mature protein into the plasma. This pre-portion of the molecule is important for the assembly of the mature vWF protein (Verwiej, L. et al., *EBMO J* 6:2885–2890 (1987); Wise, R. J. et al., *Cell* 52:229–236 (1988)). With the Scottish terrier frameshift vWD mutation, neither this pre-portion nor any of the mature factor is ever produced, in keeping with the fact that no factor has ever been detected in the blood of affected dogs.

The determination of the complete canine vWF cDNA sequence will have an impact upon the development of carrier tests for other breeds and other species as well. Currently, Shetland sheepdogs and Dutch Kooikers are known to have a significant amount of Type 3vWD (Brooks, M. et al., *JAVMA* 200:1123–1127 (1992); Slappendel, R. J., *Vet-Q* 17:S21–S22 (1995)). Type 3 vWD has occasionally be seen in other breeds as well (e.g., Johnson, G. S. et al., *JAVMA* 176:1261–1263 (1980)). All Type 3 vWD mutations described in humans to date have been found within the vWF gene itself. The availability of the canine sequence will make it easier to find the mutations in these breeds. In addition, at least some Type 1 mutations have been found within the human vWF gene, and thus Type 1 mutations may also be found within the vWF gene for breeds affected with that form of the disease. The availability of two divergent mammalian vWF cDNA sequences will also make it much easier to sequence the gene from other mammalian species using cross-species PCR methods (e.g., Venta et al., *Biochem. Genet.* (1996) in press).

The test described herein for the detection of the mutation in Scottish terriers may be performed on small amounts of DNA from any tissue. The tissues that are the least invasive to obtain are blood and buccal cells. For maximum convenience, a cheek swab as a source of DNA is preferred.

The foregoing discussion discloses and describes merely exemplary embodiments of the present invention. One skilled in the art will readily recognize from such discussion, and from the accompanying drawings, that various changes, modifications and variations can be made therein without departing from the spirit and scope of the invention.

All patents and other publications cited herein are expressly incorporated by reference.

We claim:

1. An isolated nucleic acid comprising a nucleotide sequence encoding the polypeptide of SEQ ID NO. 2, having a mutation at codon 85.

2. The isolated nucleic acid of claim 1, wherein the mutation is a deletion.

3. A vector comprising the nucleic acid of claim 1.

4. A vector comprising the nucleic acid of claim 2.

5. A cell comprising the vector of claim 3.

6. A cell comprising the vector of claim 4.

7. The isolated nucleic acid of claim 1, wherein the nucleotide sequence is capable of hybridizing under high stringency conditions to the complement of SEQ ID NO. 1 having a base deletion at codon 85.

8. A vector comprising the nucleic acid of claim 7.

9. A cell comprising the vector of claim 8.

10. A method of detecting a canine von Willebrand Factor gene in a sample comprising the steps of:

a) contacting the sample with an oligonucleotide comprising contiguous nucleotides of the nucleic acid sequence of SEQ ID NO. 1 having a base deletion at codon 85, and capable of specifically hybridizing with the canine von Willebrand Factor gene, under conditions favorable for hybridization of the oligonucleotide to any complementary sequences of nucleic acid in the sample; and b) detecting hybridization, thereby detecting a canine von Willebrand Factor gene.

11. The method of claim 10, further comprising the step of:

c) quantifying hybridization of the oligonucleotide to complementary sequence.

12. A method of detecting a canine von Willebrand Factor gene in a sample comprising the steps of:

a) contacting the sample with an oligonucleotide comprising contiguous nucleotides of the nucleic acid sequence that is complementary to the sequence of SEQ ID NO. 1 having a base deletion at codon 85, and capable of specifically hybridizing to the complementary nucleotide sequence, under conditions favorable for hybridization of the oligonucleotide to any complementary sequences of nucleic acid in the sample; and b) detecting hybridization, thereby detecting a canine von Willebrand Factor gene.

13. The method of claim 12, further comprising the step of:

c) quantifying ybidization of the oligonucleotide to complementary sequences.

14. An assay kit for screening for a canine von Willebrand Factor gene comprising:

a) an oligonucleotide comprising contiguous nucleotides from the nucleic acid sequence that is complementary to the sequence of SEQ ID NO. 1 having a base deletion at codon 85, and capable of specifically hybridizing to the complementary nucleotide sequence; and b) reagents for hybridization of the oligonucleotide to a complementary nucleic acid sequence.

15. An oligonucleotide probe capable of detecting a mutation associated with canine von Willebrand's disease, wherein the mutation is a base deletion at codon 85 of the canine von Willebrand Factor gene.

* * * * *

SEQUENCE LISTING

```
<160> NUMBER OF SEQ ID NOS: 13

<210> SEQ ID NO 1
<211> LENGTH: 8802
<212> TYPE: DNA
<213> ORGANISM: Canine
<220> FEATURE:
<221> NAME/KEY: CDS
<222> LOCATION: (203)...(8641)

<400> SEQUENCE: 1
cattaaaagg tcctggctgg gagcttttt ttgggaccag cactccatgt t caagggcaa    60 acagggcca attaggatca atcttttttc tttctttttt taaaaaaaaa a attcttccc   120 actttgcaca cggacagtag tacataccag tagctctctg cgaggacggt g atcactaat  180 catttctcct gcttcgtggc ag atg agt cct acc aga ct t gtg agg gtg ctg    232
                        Met Ser Pro Thr Arg Leu V al Arg Val Leu
                         1               5                    10 ctg gct ctg gcc ctc atc ttg cca ggg aaa c tt tgt aca aaa ggg act    280
Leu Ala Leu Ala Leu Ile Leu Pro Gly Lys L eu Cys Thr Lys Gly Thr
             15                  20                      25 gtt gga agg tca tcg atg gcc cga tgt agc c tt ctc gga ggt gac ttc    328
Val Gly Arg Ser Ser Met Ala Arg Cys Ser L eu Leu Gly Gly Asp Phe
         30                      35                  40 atc aac acc ttt gat gag agc atg tac agc t tt gcg gga gat tgc agt    376
Ile Asn Thr Phe Asp Glu Ser Met Tyr Ser P he Ala Gly Asp Cys Ser
     45                      50                  55
```

-continued

```
tac ctc ctg gct ggg gac tgc cag gaa cac t cc atc tca ctt atc ggg       424
Tyr Leu Leu Ala Gly Asp Cys Gln Glu His S er Ile Ser Leu Ile Gly
         60                  65                  70 ggt ttc caa aat gac aaa aga gtg agc ctc t cc gtg tat ctc gga gaa       472
Gly Phe Gln Asn Asp Lys Arg Val Ser Leu S er Val Tyr Leu Gly Glu
 75                  80                  85                  90 ttt ttc gac att cat ttg ttt gtc aat ggt a cc atg ctg cag ggg acc       520
Phe Phe Asp Ile His Leu Phe Val Asn Gly T hr Met Leu Gln Gly Thr
                 95                 100                 105 caa agc atc tcc atg ccc tac gcc tcc aat g gg ctg tat cta gag gcc       568
Gln Ser Ile Ser Met Pro Tyr Ala Ser Asn G ly Leu Tyr Leu Glu Ala
            110                 115                 120 gag gct ggc tac tac aag ctg tcc agt gag g cc tac ggc ttt gtg gcc       616
Glu Ala Gly Tyr Tyr Lys Leu Ser Ser Glu A la Tyr Gly Phe Val Ala
        125                 130                 135 aga att gat ggc aat ggc aac ttt caa gtc c tg ctg tca gac aga tac       664
Arg Ile Asp Gly Asn Gly Asn Phe Gln Val L eu Leu Ser Asp Arg Tyr
    140                 145                 150 ttc aac aag acc tgt ggg ctg tgt ggc aac t tt aat atc ttt gct gag       712
Phe Asn Lys Thr Cys Gly Leu Cys Gly Asn P he Asn Ile Phe Ala Glu
155                 160                 165                 170 gat gac ttc aag act caa gaa ggg acg ttg a ct tcg gac ccc tat gac       760
Asp Asp Phe Lys Thr Gln Glu Gly Thr Leu T hr Ser Asp Pro Tyr Asp
                175                 180                 185 ttt gcc aac tcc tgg gcc ctg agc agt ggg g aa caa cgg tgc aaa cgg       808
Phe Ala Asn Ser Trp Ala Leu Ser Ser Gly G lu Gln Arg Cys Lys Arg
            190                 195                 200 gtg tcc cct ccc agc agc cca tgc aat gtc t cc tct gat gaa gtg cag       856
Val Ser Pro Pro Ser Ser Pro Cys Asn Val S er Ser Asp Glu Val Gln
        205                 210                 215 cag gtc ctg tgg gag cag tgc cag ctc ctg a ag agt gcc tcg gtg ttt       904
Gln Val Leu Trp Glu Gln Cys Gln Leu Leu L ys Ser Ala Ser Val Phe
    220                 225                 230 gcc cgc tgc cac ccg ctg gtg gac cct gag c ct ttt gtc gcc ctg tgt       952
Ala Arg Cys His Pro Leu Val Asp Pro Glu P ro Phe Val Ala Leu Cys
235                 240                 245                 250 gaa agg act ctg tgc acc tgt gtc cag ggg a tg gag tgc cct tgt gcg      1000
Glu Arg Thr Leu Cys Thr Cys Val Gln Gly M et Glu Cys Pro Cys Ala
                255                 260                 265 gtc ctc ctg gag tac gcc cgg gcc tgt gcc c ag cag ggg att gtc ttg      1048
Val Leu Leu Glu Tyr Ala Arg Ala Cys Ala G ln Gln Gly Ile Val Leu
            270                 275                 280 tac ggc tgg acc gac cac agc gtc tgc cga c ca gca tgc cct gct ggc      1096
Tyr Gly Trp Thr Asp His Ser Val Cys Arg P ro Ala Cys Pro Ala Gly
        285                 290                 295 atg gag tac aag gag tgc gtg tcc cct tgc a cc aga act tgc cag agc      1144
Met Glu Tyr Lys Glu Cys Val Ser Pro Cys T hr Arg Thr Cys Gln Ser
    300                 305                 310 ctt cat gtc aaa gaa gtg tgt cag gag caa t gt gta gat ggc tgc agc      1192
Leu His Val Lys Glu Val Cys Gln Glu Gln C ys Val Asp Gly Cys Ser
315                 320                 325                 330 tgc ccc gag ggc cag ctc ctg gat gaa ggc c ac tgc gtg gga agt gct      1240
Cys Pro Glu Gly Gln Leu Leu Asp Glu Gly H is Cys Val Gly Ser Ala
                335                 340                 345 gag tgt ccc tgt gtg cat gct ggg caa cgg t ac cct ccg ggc gcc tcc      1288
Glu Cys Ser Cys Val His Ala Gly Gln Arg T yr Pro Pro Gly Ala Ser
            350                 355                 360 ctc tta cag gac tgc cac acc tgc att tgc c ga aat agc ctg tgg atc      1336
Leu Leu Gln Asp Cys His Thr Cys Ile Cys A rg Asn Ser Leu Trp Ile
```

-continued

```
                  365                    370                         375
       tgc agc aat gaa gaa tgc cca ggc gag tgt c tg gtc aca gga cag tcc         1384
       Cys Ser Asn Glu Glu Cys Pro Gly Glu Cys L eu Val Thr Gly Gln Ser
               380                 385                 390 cac ttc aag agc ttc gac aac agg tac ttc a cc ttc agt ggg gtc tgc         1432
       His Phe Lys Ser Phe Asp Asn Arg Tyr Phe T hr Phe Ser Gly Val Cys
       395                 400                 405                 410 cac tac ctg ctg gcc cag gac tgc cag gac c ac aca ttc tct gtt gtc         1480
       His Tyr Leu Leu Ala Gln Asp Cys Gln Asp H is Thr Phe Ser Val Val
                           415                 420                 425 ata gag act gtc cag tgt gcc gat gac ctg g at gct gtc tgc acc cgc         1528
       Ile Glu Thr Val Gln Cys Ala Asp Asp Leu A sp Ala Val Cys Thr Arg
                       430                 435                 440 tcg gtc acc gtc cgc ctg cct gga cat cac a ac agc ctt gtg aag ctg         1576
       Ser Val Thr Val Arg Leu Pro Gly His His A sn Ser Leu Val Lys Leu
                   445                 450                 455 aag aat ggg gga gga gtc tcc atg gat ggc c ag gat atc cag att cct         1624
       Lys Asn Gly Gly Gly Val Ser Met Asp Gly G ln Asp Ile Gln Ile Pro
               460                 465                 470 ctc ctg caa ggt gac ctc cgc atc cag cac a cc gtg atg gcc tcc gtg         1672
       Leu Leu Gln Gly Asp Leu Arg Ile Gln His T hr Val Met Ala Ser Val
       475                 480                 485                 490 cgc ctc agc tac ggg gag gac ctg cag atg g at tcg gac gtc cgg ggc         1720
       Arg Leu Ser Tyr Gly Glu Asp Leu Gln Met A sp Ser Asp Val Arg Gly
                           495                 500                 505 agg cta ctg gtg acg ctg tac ccc gcc tac g cg ggg aag acg tgc ggc         1768
       Arg Leu Leu Val Thr Leu Tyr Pro Ala Tyr A la Gly Lys Thr Cys Gly
                       510                 515                 520 cgt ggc ggg aac tac aac ggc aac cgg ggg g ac gac ttc gtg acg ccc         1816
       Arg Gly Gly Asn Tyr Asn Gly Asn Arg Gly A sp Asp Phe Val Thr Pro
                   525                 530                 535 gca ggc ctg gcg gag ccc ctg gtg gag gac t tc ggg aac gcc tgg aag         1864
       Ala Gly Leu Ala Glu Pro Leu Val Glu Asp P he Gly Asn Ala Trp Lys
               540                 545                 550 ctg ctc ggg gcc tgc gag aac ctg cag aag c ag cac cgc gat ccc tgc         1912
       Leu Leu Gly Ala Cys Glu Asn Leu Gln Lys G ln His Arg Asp Pro Cys
       555                 560                 565                 570 agc ctc aac ccg cgc cag gcc agg ttt gcg g ag gag gcg tgc gcg ctg         1960
       Ser Leu Asn Pro Arg Gln Ala Arg Phe Ala G lu Glu Ala Cys Ala Leu
                           575                 580                 585 ctg acg tcc tcg aag ttc gag ccc tgc cac c ga gcg gtg ggt cct cag         2008
       Leu Thr Ser Ser Lys Phe Glu Pro Cys His A rg Ala Val Gly Pro Gln
                       590                 595                 600 ccc tac gtg cag aac tgc ctc tac gac gtc t gc tcc tgc tcc gac ggc         2056
       Pro Tyr Val Gln Asn Cys Leu Tyr Asp Val C ys Ser Cys Ser Asp Gly
                   605                 610                 615 aga gac tgt ctt tgc agc gcc gtg gcc aac t ac gcc gca gcc gtg gcc         2104
       Arg Asp Cys Leu Cys Ser Ala Val Ala Asn T yr Ala Ala Ala Val Ala
               620                 625                 630 cgg agg ggc gtg cac atc gcg tgg cgg gag c cg ggc ttc tgt gcg ctg         2152
       Arg Arg Gly Val His Ile Ala Trp Arg Glu P ro Gly Phe Cys Ala Leu
       635                 640                 645                 650 agc tgc ccc cag ggc cag gtg tac ctg cag t gt ggg acc ccc tgc aac         2200
       Ser Cys Pro Gln Gly Gln Val Tyr Leu Gln C ys Gly Thr Pro Cys Asn
                           655                 660                 665 atg acc tgt ctc tcc ctc tct tac ccg gag g ag gac tgc aat gag gtc         2248
       Met Thr Cys Leu Ser Leu Ser Tyr Pro Glu G lu Asp Cys Asn Glu Val
                       670                 675                 680 tgc ttg gaa agc tgc ttc tcc ccc cca ggg c tg tac ctg gat gag agg         2296
```

```
                                      -continued

Cys Leu Glu Ser Cys Phe Ser Pro Gly L eu Tyr Leu Asp Glu Arg
            685                 690                  695 gga gat tgt gtg ccc aag gct cag tgt ccc t gt tac tat gat ggt gag     2344
Gly Asp Cys Val Pro Lys Ala Gln Cys Pro C ys Tyr Tyr Asp Gly Glu
        700                 705                  710 atc ttt cag ccc gaa gac atc ttc tca gac c at cac acc atg tgc tac     2392
Ile Phe Gln Pro Glu Asp Ile Phe Ser Asp H is His Thr Met Cys Tyr
715                 720                  725                  730 tgt gag gat ggc ttc atg cac tgt acc aca a gt gga ggc ctg gga agc     2440
Cys Glu Asp Gly Phe Met His Cys Thr Thr S er Gly Gly Leu Gly Ser
                735                  740                  745 ctg ctg ccc aac ccg gtg ctc agc agc ccc c gg tgt cac cgc agc aaa     2488
Leu Leu Pro Asn Pro Val Leu Ser Ser Pro A rg Cys His Arg Ser Lys
            750                  755                  760 agg agc ctg tcc tgt cgg ccc ccc atg gtc a ag ttg gtg tgt ccc gct     2536
Arg Ser Leu Ser Cys Arg Pro Pro Met Val L ys Leu Val Cys Pro Ala
        765                  770                  775 gat aac ccg agg gct gaa gga ctg gag tgt g cc aaa acc tgc cag aac     2584
Asp Asn Pro Arg Ala Glu Gly Leu Glu Cys A la Lys Thr Cys Gln Asn
    780                  785                  790 tat gac ctg cag tgc atg agc aca ggc tgt g tc tcc ggc tgc ctc tgc     2632
Tyr Asp Leu Gln Cys Met Ser Thr Gly Cys V al Ser Gly Cys Leu Cys
795                  800                  805                  810 ccg cag ggc atg gtc cgg cat gaa aac agg t gt gtg gcg ctg gaa aga     2680
Pro Gln Gly Met Val Arg His Glu Asn Arg C ys Val Ala Leu Glu Arg
                815                  820                  825 tgt ccc tgc ttc cac caa ggc caa gag tac g cc cca gga gaa acc gtg     2728
Cys Pro Cys Phe His Gln Gly Gln Glu Tyr A la Pro Gly Glu Thr Val
            830                  835                  840 aaa att gac tgc aac act tgt gtc tgt cgg g ac cgg aag tgg acc tgc     2776
Lys Ile Asp Cys Asn Thr Cys Val Cys Arg A sp Arg Lys Trp Thr Cys
        845                  850                  855 aca gac cat gtg tgt gat gcc act tgc tct g cc atc ggc atg gcg cac     2824
Thr Asp His Val Cys Asp Ala Thr Cys Ser A la Ile Gly Met Ala His
    860                  865                  870 tac ctc acc ttc gac gga ctc aag tac ctg t tc cct ggg gag tgc cag     2872
Tyr Leu Thr Phe Asp Gly Leu Lys Tyr Leu P he Pro Gly Glu Cys Gln
875                  880                  885                  890 tat gtt ctg gtg cag gat tac tgc ggc agt a ac cct ggg acc tta cgg     2920
Tyr Val Leu Val Gln Asp Tyr Cys Gly Ser A sn Pro Gly Thr Leu Arg
                895                  900                  905 atc ctg gtg ggg aac gag ggg tgc agc tac c cc tca gtg aaa tgc aag     2968
Ile Leu Val Gly Asn Glu Gly Cys Ser Tyr P ro Ser Val Lys Cys Lys
            910                  915                  920 aag cgg gtc acc atc ctg gtg gaa gga gga g ag att gaa ctg ttt gat     3016
Lys Arg Val Thr Ile Leu Val Glu Gly Gly G lu Ile Glu Leu Phe Asp
        925                  930                  935 ggg gag gtg aat gtg aag aaa ccc atg aag g at gag act cac ttt gag     3064
Gly Glu Val Asn Val Lys Lys Pro Met Lys A sp Glu Thr His Phe Glu
    940                  945                  950 gtg gta gag tct ggt cag tac gtc att ctg c tg ctg ggc aag gca ctc     3112
Val Val Glu Ser Gly Gln Tyr Val Ile Leu L eu Leu Gly Lys Ala Leu
955                  960                  965                  970 tct gtg gtc tgg gac cac cgc ctg agc atc t ct gtg acc ctg aag cgg     3160
Ser Val Val Trp Asp His Arg Leu Ser Ile S er Val Thr Leu Lys Arg
                975                  980                  985 aca tac cag gag cag gtg tgt ggc ctg tgt g gg aat ttt gat  ggc atc    3208
Thr Tyr Gln Glu Gln Val Cys Gly Leu Cys G ly Asn Phe Asp  Gly Ile
            990                  995                  1000
```

```
cag aac aat gat ttc acc agc agc agc ctc caa ata gaa gaa gac cct   3256
Gln Asn Asn Asp Phe Thr Ser Ser Ser Leu Gln Ile Glu Glu Asp Pro
             1005                1010                1015 gtg gac ttt ggg aat tcc tgg aaa gtg aac ccg cag tgt gcc gac acc   3304
Val Asp Phe Gly Asn Ser Trp Lys Val Asn Pro Gln Cys Ala Asp Thr
        1020                1025                1030 aag aaa gta cca ctg gac tca tcc cct gcc gtc tgc cac aac aac atc   3352
Lys Lys Val Pro Leu Asp Ser Ser Pro Ala Val Cys His Asn Asn Ile
1035                1040                1045                1050 atg aag cag acg atg gtg gat tcc tcc tgc agg atc ctc acc agt gat   3400
Met Lys Gln Thr Met Val Asp Ser Ser Cys Arg Ile Leu Thr Ser Asp
                1055                1060                1065 att ttc cag gac tgc aac agg ctg gtg gac cct gag cca ttc ctg gac   3448
Ile Phe Gln Asp Cys Asn Arg Leu Val Asp Pro Glu Pro Phe Leu Asp
            1070                1075                1080 att tgc atc tac gac act tgc tcc tgt gag tcc att ggg gac tgc acc   3496
Ile Cys Ile Tyr Asp Thr Cys Ser Cys Glu Ser Ile Gly Asp Cys Thr
        1085                1090                1095 tgc ttc tgt gac acc att gct gct tac gcc cac gtc tgt gcc cag cat   3544
Cys Phe Cys Asp Thr Ile Ala Ala Tyr Ala His Val Cys Ala Gln His
    1100                1105                1110 ggc aag gtg gta gcc tgg agg aca gcc aca ttc tgt ccc cag aat tgc   3592
Gly Lys Val Val Ala Trp Arg Thr Ala Thr Phe Cys Pro Gln Asn Cys
1115                1120                1125                1130 gag gag cgg aat ctc cac gag aat ggg tat gag tgt gag tgg cgc tat   3640
Glu Glu Arg Asn Leu His Glu Asn Gly Tyr Glu Cys Glu Trp Arg Tyr
                1135                1140                1145 aac agc tgt gcc cct gcc tgt ccc atc acg tgc cag cac ccc gag cca   3688
Asn Ser Cys Ala Pro Ala Cys Pro Ile Thr Cys Gln His Pro Glu Pro
            1150                1155                1160 ctg gca tgc cct gta cag tgt gtt gaa ggt tgc cat gcg cac tgc cct   3736
Leu Ala Cys Pro Val Gln Cys Val Glu Gly Cys His Ala His Cys Pro
        1165                1170                1175 cca ggg aaa atc ctg gat gag ctt ttg cag acc tgc atc gac cct gaa   3784
Pro Gly Lys Ile Leu Asp Glu Leu Leu Gln Thr Cys Ile Asp Pro Glu
    1180                1185                1190 gac tgt cct gtg tgt gag gtg gct ggt cgt cgc ttg gcc cca gga aag   3832
Asp Cys Pro Val Cys Glu Val Ala Gly Arg Arg Leu Ala Pro Gly Lys
1195                1200                1205                1210 aaa atc atc ttg aac ccc agt gac cct gag cac tgc caa att tgt aat   3880
Lys Ile Ile Leu Asn Pro Ser Asp Pro Glu His Cys Gln Ile Cys Asn
                1215                1220                1225 tgt gat ggt gtc aac ttc acc tgt aag gcc tgc aga gaa ccc gga agt   3928
Cys Asp Gly Val Asn Phe Thr Cys Lys Ala Cys Arg Glu Pro Gly Ser
            1230                1235                1240 gtt gtg gtg ccc ccc aca gat ggc ccc att ggc tct acc acc tcg tat   3976
Val Val Val Pro Pro Thr Asp Gly Pro Ile Gly Ser Thr Thr Ser Tyr
        1245                1250                1255 gtg gag gac acg tcg gag ccg ccc ctc cat gac ttc cac tgc agc agg   4024
Val Glu Asp Thr Ser Glu Pro Pro Leu His Asp Phe His Cys Ser Arg
    1260                1265                1270 ctt ctg gac ctg gtt ttc ctg ctg gat ggc tcc tcc aag ctg tct gag   4072
Leu Leu Asp Leu Val Phe Leu Leu Asp Gly Ser Ser Lys Leu Ser Glu
1275                1280                1285                1290 gac gag ttt gaa gtg ctg aag gtc ttt gtg gtg ggt atg atg gag cat   4120
Asp Glu Phe Glu Val Leu Lys Val Phe Val Val Gly Met Met Glu His
                1295                1300                1305 ctg cac atc tcc cag aag cgg atc cgc gtg gct gtg gtg gag tac cac   4168
Leu His Ile Ser Gln Lys Arg Ile Arg Val Ala Val Val Glu Tyr His
            1310                1315                1320
```

```
gac ggc tcc  cac gcc tac atc gag  ctc aag gac cgg aag  cga ccc tca    4216
Asp Gly Ser  His Ala Tyr Ile Glu  Leu Lys Asp Arg Lys  Arg Pro Ser
         1325                 1330                 1335 gag ctg cgg cgc atc acc agc  cag gtg aag tac gcg  ggc agc gag gtg     4264
Glu Leu Arg Arg Ile Thr Ser  Gln Val Lys Tyr Ala  Gly Ser Glu Val
        1340                     1345                 1350 gcc  tcc acc agt gag gtc  tta aag tac acg ctg  ttc cag atc ttt ggc    4312
Ala  Ser Thr Ser Glu Val  Leu Lys Tyr Thr Leu  Phe Gln Ile Phe Gly
1355                 1360                 1365                 1370 aag atc gac cgc ccg  gaa gcg tct cgc att  gcc ctg ctc ctg atg  gcc    4360
Lys Ile Asp Arg Pro  Glu Ala Ser Arg Ile  Ala Leu Leu Leu Met  Ala
                1375                 1380                 1385 agc cag gag ccc  tca agg ctg gcc cgg  aat ttg gtc cgc tat  gtg cag    4408
Ser Gln Glu Pro  Ser Arg Leu Ala Arg  Asn Leu Val Arg Tyr  Val Gln
            1390                 1395                 1400 ggc ctg aag  aag aag aaa gtc att  gtc atc cct gtg ggc  atc ggg ccc    4456
Gly Leu Lys  Lys Lys Lys Val Ile  Val Ile Pro Val Gly  Ile Gly Pro
         1405                 1410                 1415 cac gcc agc ctt aag cag atc  cac ctc ata gag aag  cag gcc cct gag     4504
His Ala Ser Leu Lys Gln Ile  His Leu Ile Glu Lys  Gln Ala Pro Glu
        1420                     1425                 1430 aac  aag gcc ttt gtg ttc  agt ggt gtg gat gag  ttg gag cag cga agg    4552
Asn  Lys Ala Phe Val Phe  Ser Gly Val Asp Glu  Leu Glu Gln Arg Arg
1435                 1440                 1445                 1450 gat gag att atc aac  tac ctc tgt gac ctt  gcc ccc gaa gca cct  gcc    4600
Asp Glu Ile Ile Asn  Tyr Leu Cys Asp Leu  Ala Pro Glu Ala Pro  Ala
                1455                 1460                 1465 cct act cag cac  ccc cca atg gcc cag  gtc acg gtg ggt tcg  gag ctg    4648
Pro Thr Gln His  Pro Pro Met Ala Gln  Val Thr Val Gly Ser  Glu Leu
            1470                 1475                 1480 ttg ggg gtt  tca tct cca gga ccc  aaa agg aac tcc atg  gtc ctg gat    4696
Leu Gly Val  Ser Ser Pro Gly Pro  Lys Arg Asn Ser Met  Val Leu Asp
         1485                 1490                 1495 gtg gtg ttt gtc ctg gaa ggg  tca gac aaa att ggt  gag gcc aac ttt     4744
Val Val Phe Val Leu Glu Gly  Ser Asp Lys Ile Gly  Glu Ala Asn Phe
        1500                     1505                 1510 aac  aaa agc agg gag ttc  atg gag gag gtg att  cag cgg atg gac gtg    4792
Asn  Lys Ser Arg Glu Phe  Met Glu Glu Val Ile  Gln Arg Met Asp Val
1515                 1520                 1525                 1530 ggc cag gac agg atc  cac gtc aca gtg ctg  cag tac tcg tac atg  gtg    4840
Gly Gln Asp Arg Ile  His Val Thr Val Leu  Gln Tyr Ser Tyr Met  Val
                1535                 1540                 1545 acc gtg gag tac  acc ttc agc gag gcg  cag tcc aag ggc gag  gtc cta    4888
Thr Val Glu Tyr  Thr Phe Ser Glu Ala  Gln Ser Lys Gly Glu  Val Leu
            1550                 1555                 1560 cag cag gtg  cgg gat atc cga tac  cgg ggt ggc aac agg  acc aac act    4936
Gln Gln Val  Arg Asp Ile Arg Tyr  Arg Gly Gly Asn Arg  Thr Asn Thr
         1565                 1570                 1575 gga ctg gcc ctg caa tac ctg  tcc gaa cac agc ttc  tcg gtc agc cag     4984
Gly Leu Ala Leu Gln Tyr Leu  Ser Glu His Ser Phe  Ser Val Ser Gln
        1580                     1585                 1590 ggg  gac cgg gag cag gta  cct aac ctg gtc tac  atg gtc aca gga aac    5032
Gly  Asp Arg Glu Gln Val  Pro Asn Leu Val Tyr  Met Val Thr Gly Asn
1595                 1600                 1605                 1610 ccc gct tct gat gag  atc aag cgg atg cct  gga gac atc cag gtg  gtg    5080
Pro Ala Ser Asp Glu  Ile Lys Arg Met Pro  Gly Asp Ile Gln Val  Val
                1615                 1620                 1625 ccc atc ggg gtg  ggt cca cat gcc aat  gtg cag gag ctg gag  aag att    5128
Pro Ile Gly Val  Gly Pro His Ala Asn  Val Gln Glu Leu Glu  Lys Ile
```

```
                1630              1635              1640
ggc tgg ccc aat gcc ccc atc ctc atc cat gac ttt gag atg ctc cct   5176
Gly Trp Pro Asn Ala Pro Ile Leu Ile His Asp Phe Glu Met Leu Pro
        1645              1650              1655 cga gag gct cct gat ctg gtg cta cag agg tgc tgc tct gga gag ggg   5224
Arg Glu Ala Pro Asp Leu Val Leu Gln Arg Cys Cys Ser Gly Glu Gly
        1660              1665              1670 ctg cag atc ccc acc ctc tcc ccc acc cca gat tgc agc cag ccc ctg   5272
Leu Gln Ile Pro Thr Leu Ser Pro Thr Pro Asp Cys Ser Gln Pro Leu
1675              1680              1685              1690 gat gtg gtc ctc ctc ctg gat ggc tct tcc agc att cca gct tct tac   5320
Asp Val Val Leu Leu Leu Asp Gly Ser Ser Ser Ile Pro Ala Ser Tyr
                1695              1700              1705 ttt gat gaa atg aag agc ttc acc aag gct ttt att tca aga gct aat   5368
Phe Asp Glu Met Lys Ser Phe Thr Lys Ala Phe Ile Ser Arg Ala Asn
            1710              1715              1720 ata ggg ccc cgg ctc act caa gtg tcg gtg ctg caa tat gga agc atc   5416
Ile Gly Pro Arg Leu Thr Gln Val Ser Val Leu Gln Tyr Gly Ser Ile
        1725              1730              1735 acc act atc gat gtg cct tgg aat gta gcc tat gag aaa gtc cat tta   5464
Thr Thr Ile Asp Val Pro Trp Asn Val Ala Tyr Glu Lys Val His Leu
    1740              1745              1750 ctg agc ctt gtg gac ctc atg cag cag gag gga ggc ccc agc gaa att   5512
Leu Ser Leu Val Asp Leu Met Gln Gln Glu Gly Gly Pro Ser Glu Ile
1755              1760              1765              1770 ggg gat gct ttg agc ttt gcc gtg cga tat gtc acc tca gaa gtc cat   5560
Gly Asp Ala Leu Ser Phe Ala Val Arg Tyr Val Thr Ser Glu Val His
                1775              1780              1785 ggt gcc agg ccc gga gcc tcg aaa gcg gtg gtt atc cta gtc aca gat   5608
Gly Ala Arg Pro Gly Ala Ser Lys Ala Val Val Ile Leu Val Thr Asp
            1790              1795              1800 gtc tcc gtg gat tca gtg gat gct gca gcc gag gcc gcc aga tcc aac   5656
Val Ser Val Asp Ser Val Asp Ala Ala Ala Glu Ala Ala Arg Ser Asn
        1805              1810              1815 cga gtg aca gtg ttc ccc att gga atc ggg gat cgg tac agt gag gcc   5704
Arg Val Thr Val Phe Pro Ile Gly Ile Gly Asp Arg Tyr Ser Glu Ala
    1820              1825              1830 cag ctg agc agc ttg gca ggc cca aag gct ggc tcc aat atg gta agg   5752
Gln Leu Ser Ser Leu Ala Gly Pro Lys Ala Gly Ser Asn Met Val Arg
1835              1840              1845              1850 ctc cag cga att gaa gac ctc ccc acc gtg gcc acc ctg gga aat tcc   5800
Leu Gln Arg Ile Glu Asp Leu Pro Thr Val Ala Thr Leu Gly Asn Ser
                1855              1860              1865 ttc ttc cac aag ctg tgc tct ggg ttt gat aga gtt tgc gtg gat gag   5848
Phe Phe His Lys Leu Cys Ser Gly Phe Asp Arg Val Cys Val Asp Glu
            1870              1875              1880 gat ggg aat gag aag agg ccc ggg gat gtc tgg acc ttg cca gac cag   5896
Asp Gly Asn Glu Lys Arg Pro Gly Asp Val Trp Thr Leu Pro Asp Gln
        1885              1890              1895 tgc cac aca gtg act tgc ctg cca gat ggc cag acc ttg ctg aag agt   5944
Cys His Thr Val Thr Cys Leu Pro Asp Gly Gln Thr Leu Leu Lys Ser
    1900              1905              1910 cat cgg gtc aac tgt gac cgg ggg cca agg cct tcg tgc ccc aat ggc   5992
His Arg Val Asn Cys Asp Arg Gly Pro Arg Pro Ser Cys Pro Asn Gly
1915              1920              1925              1930 cag ccc cct ctc agg gta gag gag acc tgt ggc tgc cgc tgg acc tgt   6040
Gln Pro Pro Leu Arg Val Glu Glu Thr Cys Gly Cys Arg Trp Thr Cys
                1935              1940              1945 ccc tgt gtg tgc atg ggc agc tct acc cgg cac atc gtg acc ttt gat   6088
```

-continued

```
                Pro Cys Val Cys Met Gly Ser Ser Thr Arg His Ile Val Thr Phe Asp
                        1950                1955                1960 ggg cag aat ttc aag ctg act ggc agc tgt tcg tat gtc cta ttt caa              6136
Gly Gln Asn Phe Lys Leu Thr Gly Ser Cys Ser Tyr Val Leu Phe Gln
        1965                1970                1975 aac aag gag cag gac ctg gag gtg att ctc cag aat ggt gcc tgc agc              6184
Asn Lys Glu Gln Asp Leu Glu Val Ile Leu Gln Asn Gly Ala Cys Ser
    1980                1985                1990 cct ggg gcg aag gag acc tgc atg aaa tcc att gag gtg aag cat gac              6232
Pro Gly Ala Lys Glu Thr Cys Met Lys Ser Ile Glu Val Lys His Asp
1995                2000                2005                2010 ggc ctc tca gtt gag ctc cac agt gac atg cag atg aca gtg aat ggg              6280
Gly Leu Ser Val Glu Leu His Ser Asp Met Gln Met Thr Val Asn Gly
            2015                2020                2025 aga cta gtc tcc atc cca tat gtg ggt gga gac atg gaa gtc aat gtt              6328
Arg Leu Val Ser Ile Pro Tyr Val Gly Gly Asp Met Glu Val Asn Val
        2030                2035                2040 tat ggg acc atc atg tat gag gtc aga ttc aac cat ctt ggc cac atc              6376
Tyr Gly Thr Ile Met Tyr Glu Val Arg Phe Asn His Leu Gly His Ile
    2045                2050                2055 ttc aca ttc acc ccc caa aac aat gag ttc cag ctg cag ctc agc ccc              6424
Phe Thr Phe Thr Pro Gln Asn Asn Glu Phe Gln Leu Gln Leu Ser Pro
2060                2065                2070 agg acc ttt gct tcg aag aca tat ggt ctc tgt ggg atc tgt gat gag              6472
Arg Thr Phe Ala Ser Lys Thr Tyr Gly Leu Cys Gly Ile Cys Asp Glu
2075                2080                2085                2090 aac gga gcc aat gac ttc att ctg agg gat ggg aca gtc acc aca gac              6520
Asn Gly Ala Asn Asp Phe Ile Leu Arg Asp Gly Thr Val Thr Thr Asp
            2095                2100                2105 tgg aag gca ctc atc cag gaa tgg acc gta cag cag ctt ggg aag aca              6568
Trp Lys Ala Leu Ile Gln Glu Trp Thr Val Gln Gln Leu Gly Lys Thr
        2110                2115                2120 tcc cag cct gtc cat gag gag cag tgt cct gtc tcc gaa ttc ttc cac              6616
Ser Gln Pro Val His Glu Glu Gln Cys Pro Val Ser Glu Phe Phe His
    2125                2130                2135 tgc cag gtc ctc ctc tca gaa ttg ttt gcc gag tgc cac aag gtc ctc              6664
Cys Gln Val Leu Leu Ser Glu Leu Phe Ala Glu Cys His Lys Val Leu
    2140                2145                2150 gct cca gcc acc ttt tat gcc atg tgc cag ccc gac agt tgc cac ccg              6712
Ala Pro Ala Thr Phe Tyr Ala Met Cys Gln Pro Asp Ser Cys His Pro
2155                2160                2165                2170 aag aaa gtg tgt gag gcg att gcc ttg tat gcc cac ctc tgt cgg acc              6760
Lys Lys Val Cys Glu Ala Ile Ala Leu Tyr Ala His Leu Cys Arg Thr
            2175                2180                2185 aaa ggg gtc tgt gtg gac tgg agg agg gcc aat ttc tgt gct atg tca              6808
Lys Gly Val Cys Val Asp Trp Arg Arg Ala Asn Phe Cys Ala Met Ser
        2190                2195                2200 tgt cca cca tcc ctg gtg tac aac cac tgt gag cat ggc tgc cct cgg              6856
Cys Pro Pro Ser Leu Val Tyr Asn His Cys Glu His Gly Cys Pro Arg
    2205                2210                2215 ctc tgt gaa ggc aat aca agc tcc tgt ggg gac caa ccc tcg gaa ggc              6904
Leu Cys Glu Gly Asn Thr Ser Ser Cys Gly Asp Gln Pro Ser Glu Gly
    2220                2225                2230 tgc ttc tgc ccc cca aac caa gtc atg ctg gaa ggt agc tgt gtc ccc              6952
Cys Phe Cys Pro Pro Asn Gln Val Met Leu Glu Gly Ser Cys Val Pro
2235                2240                2245                2250 gag gag gcc tgt acc cag tgc atc agc gag gat gga gtc cgg cac cag              7000
Glu Glu Ala Cys Thr Gln Cys Ile Ser Glu Asp Gly Val Arg His Gln
            2255                2260                2265
```

```
ttc ctg gaa acc tgg gtc cca gcc cac cag cct tgc cag atc tgc acg    7048
Phe Leu Glu Thr Trp Val Pro Ala His Gln Pro Cys Gln Ile Cys Thr
        2270                2275                2280 tgc ctc agt ggg cgg aag gtc aac tgt acg ttg cag ccc tgc ccc aca    7096
Cys Leu Ser Gly Arg Lys Val Asn Cys Thr Leu Gln Pro Cys Pro Thr
        2285                2290                2295 gcc aaa gct ccc acc tgt ggc ccg tgt gaa gtg gcc cgc ctc cgc cag    7144
Ala Lys Ala Pro Thr Cys Gly Pro Cys Glu Val Ala Arg Leu Arg Gln
        2300                2305                2310 aac gca gtg cag tgc tgc ccg gag tac gag tgt gtg tgt gac ctg gtg    7192
Asn Ala Val Gln Cys Cys Pro Glu Tyr Glu Cys Val Cys Asp Leu Val
2315                2320                2325                2330 agc tgt gac ctg ccc ccg gtg cct ccc tgc gaa gat ggc ctc cag atg    7240
Ser Cys Asp Leu Pro Pro Val Pro Pro Cys Glu Asp Gly Leu Gln Met
        2335                2340                2345 acc ctg acc aat cct ggc gag tgc aga ccc aac ttc acc tgt gcc tgc    7288
Thr Leu Thr Asn Pro Gly Glu Cys Arg Pro Asn Phe Thr Cys Ala Cys
        2350                2355                2360 agg aag gat gaa tgc aga cgg gag tcc ccg ccc tct tgt ccc ccg cac    7336
Arg Lys Asp Glu Cys Arg Arg Glu Ser Pro Pro Ser Cys Pro Pro His
        2365                2370                2375 cgg acg ccg gcc ctt cgg aag act cag tgc tgt gat gag tat gag tgt    7384
Arg Thr Pro Ala Leu Arg Lys Thr Gln Cys Cys Asp Glu Tyr Glu Cys
        2380                2385                2390 gca tgc aac tgt gtc aac tcc acg gtg agc tgc ccg ctt ggg tac ctg    7432
Ala Cys Asn Cys Val Asn Ser Thr Val Ser Cys Pro Leu Gly Tyr Leu
2395                2400                2405                2410 gcc tcg gct gtc acc aac gac tgt ggc tgc acc aca aca acc tgc ttc    7480
Ala Ser Ala Val Thr Asn Asp Cys Gly Cys Thr Thr Thr Thr Cys Phe
        2415                2420                2425 cct gac aag gtg tgt gtc cac cga ggc acc atc tac cct gtg ggc cag    7528
Pro Asp Lys Val Cys Val His Arg Gly Thr Ile Tyr Pro Val Gly Gln
        2430                2435                2440 ttc tgg gag gag gcc tgt gac gtg tgc acc tgc acg gac ttg gag gac    7576
Phe Trp Glu Glu Ala Cys Asp Val Cys Thr Cys Thr Asp Leu Glu Asp
        2445                2450                2455 tct gtg atg ggc ctg cgt gtg gcc cag tgc tcc cag aag ccc tgt gag    7624
Ser Val Met Gly Leu Arg Val Ala Gln Cys Ser Gln Lys Pro Cys Glu
        2460                2465                2470 gac aac tgc ctg tca ggc ttc act tat gtc ctt cat gaa ggc gag tgc    7672
Asp Asn Cys Leu Ser Gly Phe Thr Tyr Val Leu His Glu Gly Glu Cys
2475                2480                2485                2490 tgt gga agg tgt ctg cca tct gcc tgt gag gtg gtc act ggt tca cca    7720
Cys Gly Arg Cys Leu Pro Ser Ala Cys Glu Val Val Thr Gly Ser Pro
        2495                2500                2505 cgg ggc gac gcc cag tct cac tgg aag aat gtt ggc tct cac tgg gcc    7768
Arg Gly Asp Ala Gln Ser His Trp Lys Asn Val Gly Ser His Trp Ala
        2510                2515                2520 tcc cct gac aac ccc tgc ctc atc aat gag tgt gtc cga gtg aag gaa    7816
Ser Pro Asp Asn Pro Cys Leu Ile Asn Glu Cys Val Arg Val Lys Glu
        2525                2530                2535 gag gtc ttt gtg caa cag agg aat gtc tcc tgc ccc cag ctg aat gtc    7864
Glu Val Phe Val Gln Gln Arg Asn Val Ser Cys Pro Gln Leu Asn Val
        2540                2545                2550 ccc acc tgc ccc acg ggc ttc cag ctg agc tgt aag acc tca gag tgt    7912
Pro Thr Cys Pro Thr Gly Phe Gln Leu Ser Cys Lys Thr Ser Glu Cys
2555                2560                2565                2570 tgt ccc acc tgt cac tgc gag ccc ctg gag gcc tgc ttg ctc aat ggt    7960
Cys Pro Thr Cys His Cys Glu Pro Leu Glu Ala Cys Leu Leu Asn Gly
        2575                2580                2585
```

```
acc atc att ggg ccg ggg aaa agt ctg atg att gat gtg tgt aca acc   8008
Thr Ile Ile Gly Pro Gly Lys Ser Leu Met Ile Asp Val Cys Thr Thr
        2590                2595                2600 tgc cgc tgc acc gtg ccg gtg gga gtc atc tct gga ttc aag ctg gag   8056
Cys Arg Cys Thr Val Pro Val Gly Val Ile Ser Gly Phe Lys Leu Glu
            2605                2610                2615 ggc agg aag acc acc tgt gag gca tgc ccc ctg ggt tat aag gaa gag   8104
Gly Arg Lys Thr Thr Cys Glu Ala Cys Pro Leu Gly Tyr Lys Glu Glu
        2620                2625                2630 aag aac caa ggt gaa tgc tgt ggg aga tgt ctg cct ata gct tgc acc   8152
Lys Asn Gln Gly Glu Cys Cys Gly Arg Cys Leu Pro Ile Ala Cys Thr
2635                2640                2645                2650 att cag cta aga gga gga cag atc atg aca ctg aag cgt gat gag act   8200
Ile Gln Leu Arg Gly Gly Gln Ile Met Thr Leu Lys Arg Asp Glu Thr
            2655                2660                2665 atc cag gat ggc tgt gac agt cac ttc tgc aag gtc aat gaa aga gga   8248
Ile Gln Asp Gly Cys Asp Ser His Phe Cys Lys Val Asn Glu Arg Gly
        2670                2675                2680 gag tac atc tgg gag aag aga gtc acg ggt tgc cca cct ttc gat gaa   8296
Glu Tyr Ile Trp Glu Lys Arg Val Thr Gly Cys Pro Pro Phe Asp Glu
        2685                2690                2695 cac aag tgt ctg gct gag gga gga aaa atc atg aaa att cca ggc acc   8344
His Lys Cys Leu Ala Glu Gly Gly Lys Ile Met Lys Ile Pro Gly Thr
            2700                2705                2710 tgc tgt gac aca tgt gag gag cca gaa tgc aag gat atc att gcc aag   8392
Cys Cys Asp Thr Cys Glu Glu Pro Glu Cys Lys Asp Ile Ile Ala Lys
2715                2720                2725                2730 ctg cag cgt gtc aaa gtg gga gac tgt aag tct gaa gag gaa gtg gac   8440
Leu Gln Arg Val Lys Val Gly Asp Cys Lys Ser Glu Glu Glu Val Asp
            2735                2740                2745 att cat tac tgt gag ggt aaa tgt gcc agc aaa gcc gtg tac tcc atc   8488
Ile His Tyr Cys Glu Gly Lys Cys Ala Ser Lys Ala Val Tyr Ser Ile
        2750                2755                2760 cac atg gag gat gtg cag gac cag tgc tcc tgc tgc tcg ccc acc cag   8536
His Met Glu Asp Val Gln Asp Gln Cys Ser Cys Cys Ser Pro Thr Gln
            2765                2770                2775 acg gag ccc atg cag gtg gcc ctg cgc tgc acc aat ggc tcc ctc atc   8584
Thr Glu Pro Met Gln Val Ala Leu Arg Cys Thr Asn Gly Ser Leu Ile
        2780                2785                2790 tac cat gag atc ctc aat gcc atc gaa tgc agg tgt tcc ccc agg aag   8632
Tyr His Glu Ile Leu Asn Ala Ile Glu Cys Arg Cys Ser Pro Arg Lys
2795                2800                2805                2810 tgc agc aag tgaggccact gcctggatgc tactgtcgcc tgccttac cc          8681
Cys Ser Lys gacctcactg gactggccag agtgctgctc agtcctcctc agtcctcctc c tgctctgct   8741 cttgtgcttc ctgatcccac aataaaggtc aatctttcac cttgaaaaaa a aaaaaaaa   8801 a                                                                   8802

<210> SEQ ID NO 2
<211> LENGTH: 2813
<212> TYPE: PRT
<213> ORGANISM: Canine

<400> SEQUENCE: 2

Met Ser Pro Thr Arg Leu Val Arg Val Leu Leu Ala Leu Ala Leu Ile
 1               5                   10                  15

Leu Pro Gly Lys Leu Cys Thr Lys Gly Thr Val Gly Arg Ser Ser Met
            20                  25                  30
```

-continued

```
Ala Arg Cys Ser Leu Leu Gly Gly Asp Phe Ile Asn Thr Phe Asp Glu
        35                  40                  45
Ser Met Tyr Ser Phe Ala Gly Asp Cys Ser Tyr Leu Leu Ala Gly Asp
    50                  55                  60
Cys Gln Glu His Ser Ile Ser Leu Ile Gly Gly Phe Gln Asn Asp Lys
65                  70                  75                  80
Arg Val Ser Leu Ser Val Tyr Leu Gly Glu Phe Phe Asp Ile His Leu
                85                  90                  95
Phe Val Asn Gly Thr Met Leu Gln Gly Thr Gln Ser Ile Ser Met Pro
            100                 105                 110
Tyr Ala Ser Asn Gly Leu Tyr Leu Glu Ala Glu Ala Gly Tyr Tyr Lys
        115                 120                 125
Leu Ser Ser Glu Ala Tyr Gly Phe Val Ala Arg Ile Asp Gly Asn Gly
    130                 135                 140
Asn Phe Gln Val Leu Leu Ser Asp Arg Tyr Phe Asn Lys Thr Cys Gly
145                 150                 155                 160
Leu Cys Gly Asn Phe Asn Ile Phe Ala Glu Asp Asp Phe Lys Thr Gln
                165                 170                 175
Glu Gly Thr Leu Thr Ser Asp Pro Tyr Asp Phe Ala Asn Ser Trp Ala
            180                 185                 190
Leu Ser Ser Gly Glu Gln Arg Cys Lys Arg Val Ser Pro Pro Ser Ser
        195                 200                 205
Pro Cys Asn Val Ser Ser Asp Glu Val Gln Gln Val Leu Trp Glu Gln
    210                 215                 220
Cys Gln Leu Leu Lys Ser Ala Ser Val Phe Ala Arg Cys His Pro Leu
225                 230                 235                 240
Val Asp Pro Glu Pro Phe Val Ala Leu Cys Glu Arg Thr Leu Cys Thr
                245                 250                 255
Cys Val Gln Gly Met Glu Cys Pro Cys Ala Val Leu Leu Glu Tyr Ala
            260                 265                 270
Arg Ala Cys Ala Gln Gln Gly Ile Val Leu Tyr Gly Trp Thr Asp His
        275                 280                 285
Ser Val Cys Arg Pro Ala Cys Pro Ala Gly Met Glu Tyr Lys Glu Cys
    290                 295                 300
Val Ser Pro Cys Thr Arg Thr Cys Gln Ser Leu His Val Lys Glu Val
305                 310                 315                 320
Cys Gln Glu Gln Cys Val Asp Gly Cys Ser Cys Pro Glu Gly Gln Leu
                325                 330                 335
Leu Asp Glu Gly His Cys Val Gly Ser Ala Glu Cys Ser Cys Val His
            340                 345                 350
Ala Gly Gln Arg Tyr Pro Pro Gly Ala Ser Leu Leu Gln Asp Cys His
        355                 360                 365
Thr Cys Ile Cys Arg Asn Ser Leu Trp Ile Cys Ser Asn Glu Glu Cys
    370                 375                 380
Pro Gly Glu Cys Leu Val Thr Gly Gln Ser His Phe Lys Ser Phe Asp
385                 390                 395                 400
Asn Arg Tyr Phe Thr Phe Ser Gly Val Cys His Tyr Leu Leu Ala Gln
                405                 410                 415
Asp Cys Gln Asp His Thr Phe Ser Val Val Ile Glu Thr Val Gln Cys
            420                 425                 430
Ala Asp Asp Leu Asp Ala Val Cys Thr Arg Ser Val Thr Val Arg Leu
        435                 440                 445
```

```
Pro Gly His His Asn Ser Leu Val Lys Leu Lys Asn Gly Gly Gly Val
    450                 455                 460

Ser Met Asp Gly Gln Asp Ile Gln Ile Pro Leu Leu Gln Gly Asp Leu
465                 470                 475                 480

Arg Ile Gln His Thr Val Met Ala Ser Val Arg Leu Ser Tyr Gly Glu
                    485                 490                 495

Asp Leu Gln Met Asp Ser Asp Val Arg Gly Arg Leu Leu Val Thr Leu
                500                 505                 510

Tyr Pro Ala Tyr Ala Gly Lys Thr Cys Gly Arg Gly Gly Asn Tyr Asn
            515                 520                 525

Gly Asn Arg Gly Asp Asp Phe Val Thr Pro Ala Gly Leu Ala Glu Pro
        530                 535                 540

Leu Val Glu Asp Phe Gly Asn Ala Trp Lys Leu Leu Gly Ala Cys Glu
545                 550                 555                 560

Asn Leu Gln Lys Gln His Arg Asp Pro Cys Ser Leu Asn Pro Arg Gln
                565                 570                 575

Ala Arg Phe Ala Glu Glu Ala Cys Ala Leu Leu Thr Ser Ser Lys Phe
            580                 585                 590

Glu Pro Cys His Arg Ala Val Gly Pro Gln Pro Tyr Val Gln Asn Cys
        595                 600                 605

Leu Tyr Asp Val Cys Ser Cys Ser Asp Gly Arg Asp Cys Leu Cys Ser
    610                 615                 620

Ala Val Ala Asn Tyr Ala Ala Ala Val Ala Arg Arg Gly Val His Ile
625                 630                 635                 640

Ala Trp Arg Glu Pro Gly Phe Cys Ala Leu Ser Cys Pro Gln Gly Gln
                645                 650                 655

Val Tyr Leu Gln Cys Gly Thr Pro Cys Asn Met Thr Cys Leu Ser Leu
            660                 665                 670

Ser Tyr Pro Glu Glu Asp Cys Asn Glu Val Cys Leu Glu Ser Cys Phe
        675                 680                 685

Ser Pro Pro Gly Leu Tyr Leu Asp Glu Arg Gly Asp Cys Val Pro Lys
    690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Thr Ser Gly Gly Leu Gly Ser Leu Leu Pro Asn Pro Val
            740                 745                 750

Leu Ser Ser Pro Arg Cys His Arg Ser Lys Arg Ser Leu Ser Cys Arg
        755                 760                 765

Pro Pro Met Val Lys Leu Val Cys Pro Ala Asp Asn Pro Arg Ala Glu
    770                 775                 780

Gly Leu Glu Cys Ala Lys Thr Cys Gln Asn Tyr Asp Leu Gln Cys Met
785                 790                 795                 800

Ser Thr Gly Cys Val Ser Gly Cys Leu Cys Pro Gln Gly Met Val Arg
                805                 810                 815

His Glu Asn Arg Cys Val Ala Leu Glu Arg Cys Pro Cys Phe His Gln
            820                 825                 830

Gly Gln Glu Tyr Ala Pro Gly Glu Thr Val Lys Ile Asp Cys Asn Thr
        835                 840                 845

Cys Val Cys Arg Asp Arg Lys Trp Thr Cys Thr Asp His Val Cys Asp
    850                 855                 860

Ala Thr Cys Ser Ala Ile Gly Met Ala His Tyr Leu Thr Phe Asp Gly
```

```
865                 870                 875                 880
Leu Lys Tyr Leu Phe Pro Gly Glu Cys Gln Tyr Val Leu Val Gln Asp
                885                 890                 895
Tyr Cys Gly Ser Asn Pro Gly Thr Leu Arg Ile Leu Val Gly Asn Glu
        900                 905                 910
Gly Cys Ser Tyr Pro Ser Val Lys Cys Lys Arg Val Thr Ile Leu
        915                 920                 925
Val Glu Gly Gly Glu Ile Glu Leu Phe Asp Gly Glu Val Asn Val Lys
        930                 935                 940
Lys Pro Met Lys Asp Glu Thr His Phe Glu Val Val Glu Ser Gly Gln
945                 950                 955                 960
Tyr Val Ile Leu Leu Gly Lys Ala Leu Ser Val Val Trp Asp His
            965                 970                 975
Arg Leu Ser Ile Ser Val Thr Leu Lys Arg Thr Tyr Gln Glu Gln Val
            980                 985                 990
Cys Gly Leu Cys Gly Asn Phe Asp Gly Ile Gln Asn Asn Asp Phe Thr
            995                 1000                1005
Ser Ser Ser Leu Gln Ile Glu Asp Pro Val Asp Phe Gly Asn Ser
    1010                1015                1020
Trp Lys Val Asn Pro Gln Cys Ala Asp Thr Lys Lys Val Pro Leu Asp
1025                1030                1035                1040
Ser Ser Pro Ala Val Cys His Asn Asn Ile Met Lys Gln Thr Met Val
                1045                1050                1055
Asp Ser Ser Cys Arg Ile Leu Thr Ser Asp Ile Phe Gln Asp Cys Asn
                1060                1065                1070
Arg Leu Val Asp Pro Glu Pro Phe Leu Asp Ile Cys Ile Tyr Asp Thr
            1075                1080                1085
Cys Ser Cys Glu Ser Ile Gly Asp Cys Thr Cys Phe Cys Asp Thr Ile
    1090                1095                1100
Ala Ala Tyr Ala His Val Cys Ala Gln His Gly Lys Val Val Ala Trp
1105                1110                1115                1120
Arg Thr Ala Thr Phe Cys Pro Gln Asn Cys Glu Glu Arg Asn Leu His
                1125                1130                1135
Glu Asn Gly Tyr Glu Cys Glu Trp Arg Tyr Asn Ser Cys Ala Pro Ala
                1140                1145                1150
Cys Pro Ile Thr Cys Gln His Pro Glu Pro Leu Ala Cys Pro Val Gln
            1155                1160                1165
Cys Val Glu Gly Cys His Ala His Cys Pro Pro Gly Lys Ile Leu Asp
    1170                1175                1180
Glu Leu Leu Gln Thr Cys Ile Asp Pro Glu Asp Cys Pro Val Cys Glu
1185                1190                1195                1200
Val Ala Gly Arg Arg Leu Ala Pro Gly Lys Lys Ile Ile Leu Asn Pro
                1205                1210                1215
Ser Asp Pro Glu His Cys Gln Ile Cys Asn Cys Asp Gly Val Asn Phe
                1220                1225                1230
Thr Cys Lys Ala Cys Arg Glu Pro Gly Ser Val Val Val Pro Pro Thr
        1235                1240                1245
Asp Gly Pro Ile Gly Ser Thr Thr Ser Tyr Val Glu Asp Thr Ser Glu
    1250                1255                1260
Pro Pro Leu His Asp Phe His Cys Ser Arg Leu Leu Asp Leu Val Phe
1265                1270                1275                1280
Leu Leu Asp Gly Ser Ser Lys Leu Ser Glu Asp Glu Phe Glu Val Leu
            1285                1290                1295
```

-continued

```
Lys Val Phe Val Val Gly Met Met Glu His Leu His Ile Ser Gln Lys
            1300                1305                1310
Arg Ile Arg Val Ala Val Val Glu Tyr His Asp Gly Ser His Ala Tyr
            1315                1320                1325
Ile Glu Leu Lys Asp Arg Lys Arg Pro Ser Glu Leu Arg Arg Ile Thr
            1330                1335                1340
Ser Gln Val Lys Tyr Ala Gly Ser Glu Val Ala Ser Thr Ser Glu Val
1345                1350                1355                1360
Leu Lys Tyr Thr Leu Phe Gln Ile Phe Gly Lys Ile Asp Arg Pro Glu
            1365                1370                1375
Ala Ser Arg Ile Ala Leu Leu Leu Met Ala Ser Gln Glu Pro Ser Arg
            1380                1385                1390
Leu Ala Arg Asn Leu Val Arg Tyr Val Gln Gly Leu Lys Lys Lys Lys
            1395                1400                1405
Val Ile Val Ile Pro Val Gly Ile Gly Pro His Ala Ser Leu Lys Gln
            1410                1415                1420
Ile His Leu Ile Glu Lys Gln Ala Pro Glu Asn Lys Ala Phe Val Phe
1425                1430                1435                1440
Ser Gly Val Asp Glu Leu Glu Gln Arg Arg Asp Glu Ile Ile Asn Tyr
            1445                1450                1455
Leu Cys Asp Leu Ala Pro Glu Ala Pro Ala Pro Thr Gln His Pro Pro
            1460                1465                1470
Met Ala Gln Val Thr Val Gly Ser Glu Leu Leu Gly Val Ser Ser Pro
            1475                1480                1485
Gly Pro Lys Arg Asn Ser Met Val Leu Asp Val Val Phe Val Leu Glu
            1490                1495                1500
Gly Ser Asp Lys Ile Gly Glu Ala Asn Phe Asn Lys Ser Arg Glu Phe
1505                1510                1515                1520
Met Glu Glu Val Ile Gln Arg Met Asp Val Gly Gln Asp Arg Ile His
            1525                1530                1535
Val Thr Val Leu Gln Tyr Ser Tyr Met Val Thr Val Glu Tyr Thr Phe
            1540                1545                1550
Ser Glu Ala Gln Ser Lys Gly Glu Val Leu Gln Gln Val Arg Asp Ile
            1555                1560                1565
Arg Tyr Arg Gly Gly Asn Arg Thr Asn Thr Gly Leu Ala Leu Gln Tyr
            1570                1575                1580
Leu Ser Glu His Ser Phe Ser Val Ser Gln Gly Asp Arg Glu Gln Val
1585                1590                1595                1600
Pro Asn Leu Val Tyr Met Val Thr Gly Asn Pro Ala Ser Asp Glu Ile
            1605                1610                1615
Lys Arg Met Pro Gly Asp Ile Gln Val Val Pro Ile Gly Val Gly Pro
            1620                1625                1630
His Ala Asn Val Gln Glu Leu Glu Lys Ile Gly Trp Pro Asn Ala Pro
            1635                1640                1645
Ile Leu Ile His Asp Phe Glu Met Leu Pro Arg Glu Ala Pro Asp Leu
            1650                1655                1660
Val Leu Gln Arg Cys Cys Ser Gly Glu Gly Leu Gln Ile Pro Thr Leu
1665                1670                1675                1680
Ser Pro Thr Pro Asp Cys Ser Gln Pro Leu Asp Val Val Leu Leu Leu
            1685                1690                1695
Asp Gly Ser Ser Ser Ile Pro Ala Ser Tyr Phe Asp Glu Met Lys Ser
            1700                1705                1710
```

-continued

```
Phe Thr Lys Ala Phe Ile Ser Arg Ala Asn Ile Gly Pro Arg Leu Thr
        1715                1720                1725
Gln Val Ser Val Leu Gln Tyr Gly Ser Ile Thr Thr Ile Asp Val Pro
    1730                1735                1740
Trp Asn Val Ala Tyr Glu Lys Val His Leu Leu Ser Leu Val Asp Leu
1745                1750                1755                1760
Met Gln Gln Glu Gly Gly Pro Ser Glu Ile Gly Asp Ala Leu Ser Phe
            1765                1770                1775
Ala Val Arg Tyr Val Thr Ser Glu Val His Gly Ala Arg Pro Gly Ala
        1780                1785                1790
Ser Lys Ala Val Val Ile Leu Val Thr Asp Val Ser Val Asp Ser Val
        1795                1800                1805
Asp Ala Ala Glu Ala Ala Arg Ser Asn Arg Val Thr Val Phe Pro
    1810                1815                1820
Ile Gly Ile Gly Asp Arg Tyr Ser Glu Ala Gln Leu Ser Ser Leu Ala
1825                1830                1835                1840
Gly Pro Lys Ala Gly Ser Asn Met Val Arg Leu Gln Arg Ile Glu Asp
            1845                1850                1855
Leu Pro Thr Val Ala Thr Leu Gly Asn Ser Phe Phe His Lys Leu Cys
            1860                1865                1870
Ser Gly Phe Asp Arg Val Cys Val Asp Glu Asp Gly Asn Glu Lys Arg
        1875                1880                1885
Pro Gly Asp Val Trp Thr Leu Pro Asp Gln Cys His Thr Val Thr Cys
    1890                1895                1900
Leu Pro Asp Gly Gln Thr Leu Leu Lys Ser His Arg Val Asn Cys Asp
1905                1910                1915                1920
Arg Gly Pro Arg Pro Ser Cys Pro Asn Gly Gln Pro Pro Leu Arg Val
            1925                1930                1935
Glu Glu Thr Cys Gly Cys Arg Trp Thr Cys Pro Cys Val Cys Met Gly
        1940                1945                1950
Ser Ser Thr Arg His Ile Val Thr Phe Asp Gly Gln Asn Phe Lys Leu
        1955                1960                1965
Thr Gly Ser Cys Ser Tyr Val Leu Phe Gln Asn Lys Glu Gln Asp Leu
    1970                1975                1980
Glu Val Ile Leu Gln Asn Gly Ala Cys Ser Pro Gly Ala Lys Glu Thr
1985                1990                1995                2000
Cys Met Lys Ser Ile Glu Val Lys His Asp Gly Leu Ser Val Glu Leu
            2005                2010                2015
His Ser Asp Met Gln Met Thr Val Asn Gly Arg Leu Val Ser Ile Pro
            2020                2025                2030
Tyr Val Gly Gly Asp Met Glu Val Asn Val Tyr Gly Thr Ile Met Tyr
        2035                2040                2045
Glu Val Arg Phe Asn His Leu Gly His Ile Phe Thr Phe Thr Pro Gln
        2050                2055                2060
Asn Asn Glu Phe Gln Leu Gln Leu Ser Pro Arg Thr Phe Ala Ser Lys
2065                2070                2075                2080
Thr Tyr Gly Leu Cys Gly Ile Cys Asp Glu Asn Gly Ala Asn Asp Phe
            2085                2090                2095
Ile Leu Arg Asp Gly Thr Val Thr Thr Asp Trp Lys Ala Leu Ile Gln
        2100                2105                2110
Glu Trp Thr Val Gln Gln Leu Gly Lys Thr Ser Gln Pro Val His Glu
        2115                2120                2125
Glu Gln Cys Pro Val Ser Glu Phe Phe His Cys Gln Val Leu Leu Ser
```

-continued

```
            2130                2135                2140
Glu  Leu Phe Ala Glu  Cys His Lys Val  Leu Ala Pro Ala  Thr Phe Tyr
2145                2150                2155                2160
Ala Met Cys Gln Pro  Asp Ser Cys His Pro  Lys Lys Val Cys Glu  Ala
                2165                2170                2175
Ile Ala Leu Tyr  Ala His Leu Cys Arg  Thr Lys Gly Val  Cys Val Asp
            2180                2185                2190
Trp Arg Arg  Ala Asn Phe Cys Ala  Met Ser Cys Pro Pro  Ser Leu Val
        2195                2200                2205
Tyr Asn  His Cys Glu  His Gly  Cys Pro Arg Leu  Cys Glu Gly Asn  Thr
        2210                2215                2220
Ser  Ser Cys Gly Asp  Gln  Pro Ser Glu Gly  Cys Phe Cys Pro  Asn
2225                2230                2235                2240
Gln Val Met Leu Glu  Gly Ser Cys Val Pro  Glu Glu Ala Cys Thr  Gln
                2245                2250                2255
Cys Ile Ser Glu  Asp Gly Val Arg His  Gln Phe Leu Glu Thr  Trp Val
            2260                2265                2270
Pro Ala His  Gln Pro  Cys Gln Ile  Cys Thr Cys Leu Ser  Gly Arg Lys
        2275                2280                2285
Val Asn  Cys Thr Leu Gln Pro  Cys Pro Thr Ala Lys  Ala Pro Thr  Cys
        2290                2295                2300
Gly  Pro Cys Glu Val  Ala  Arg Leu Arg Gln  Asn  Ala Val Gln Cys  Cys
2305                2310                2315                2320
Pro Glu Tyr Glu  Cys  Val Cys Asp Leu Val  Ser Cys Asp Leu Pro  Pro
                2325                2330                2335
Val Pro Pro Cys  Glu Asp Gly Leu Gln  Met Thr Leu Thr Asn  Pro Gly
            2340                2345                2350
Glu Cys Arg  Pro Asn Phe Thr Cys  Ala Cys Arg Lys Asp  Glu Cys Arg
        2355                2360                2365
Arg Glu  Ser Pro Pro Ser Cys  Pro Pro His Arg  Thr  Pro Ala Leu  Arg
        2370                2375                2380
Lys  Thr Gln Cys Cys  Asp  Glu Tyr Glu Cys  Ala  Cys Asn Cys Val  Asn
2385                2390                2395                2400
Ser Thr Val Ser Cys  Pro Leu Gly Tyr Leu  Ala Ser Ala Val Thr  Asn
                2405                2410                2415
Asp Cys Gly Cys  Thr Thr Thr Thr Cys  Phe Pro Asp Lys Val  Cys Val
            2420                2425                2430
His Arg Gly  Thr Ile Tyr Pro Val  Gly Gln Phe Trp Glu  Glu Ala Cys
        2435                2440                2445
Asp Val  Cys Thr Cys Thr Asp  Leu Glu Asp Ser Val  Met Gly Leu Arg
        2450                2455                2460
Val  Ala Gln Cys Ser Gln  Lys Pro Cys Glu Asp  Asn Cys Leu Ser  Gly
2465                2470                2475                2480
Phe Thr Tyr Val Leu  His Glu Gly Glu Cys  Cys Gly Arg Cys Leu  Pro
                2485                2490                2495
Ser Ala Cys Glu  Val Val Thr Gly Ser  Pro Arg Gly Asp Ala  Gln Ser
            2500                2505                2510
His Trp Lys  Asn Val Gly Ser His  Trp Ala Ser Pro Asp  Asn Pro Cys
        2515                2520                2525
Leu Ile  Asn Glu Cys Val Arg  Val Lys Glu Glu Val  Phe Val Gln Gln
        2530                2535                2540
Arg Asn Val Ser Cys  Pro Gln Leu Asn Val  Pro Thr Cys Pro Thr  Gly
2545                2550                2555                2560
```

```
Phe Gln Leu Ser Cys  Lys Thr Ser Glu Cys  Cys Pro Thr Cys His  Cys
            2565                2570                2575

Glu Pro Leu Glu  Ala Cys Leu Leu Asn  Gly Thr Ile Ile Gly  Pro Gly
      2580                2585                2590

Lys Ser Leu  Met Ile Asp Val Cys  Thr Thr Cys Arg Cys  Thr Val Pro
       2595                2600                2605

Val Gly  Val Ile Ser Gly Phe  Lys Leu Glu Gly Arg  Lys Thr Thr Cys
    2610                2615                2620

Glu  Ala Cys Pro Leu Gly  Tyr Lys Glu Glu Lys  Asn Gln Gly Glu Cys
2625                2630                2635                2640

Cys Gly Arg Cys Leu  Pro Ile Ala Cys Thr  Ile Gln Leu Arg Gly  Gly
            2645                2650                2655

Gln Ile Met Thr  Leu Lys Arg Asp Glu  Thr Ile Gln Asp Gly  Cys Asp
       2660                2665                2670

Ser His Phe  Cys Lys Val Asn Glu  Arg Gly Glu Tyr Ile  Trp Glu Lys
       2675                2680                2685

Arg Val  Thr Gly Cys Pro Pro  Phe Asp Glu His Lys  Cys Leu Ala Glu
    2690                2695                2700

Gly  Gly Lys Ile Met Lys  Ile Pro Gly Thr Cys  Cys Asp Thr Cys Glu
2705                2710                2715                2720

Glu Pro Glu Cys Lys  Asp Ile Ile Ala Lys  Leu Gln Arg Val Lys  Val
            2725                2730                2735

Gly Asp Cys Lys  Ser Glu Glu Glu Val  Asp Ile His Tyr Cys  Glu Gly
       2740                2745                2750

Lys Cys Ala  Ser Lys Ala Val Tyr  Ser Ile His Met Glu  Asp Val Gln
       2755                2760                2765

Asp Gln  Cys Ser Cys Cys Ser  Pro Thr Gln Thr Glu  Pro Met Gln Val
    2770                2775                2780

Ala  Leu Arg Cys Thr Asn  Gly Ser Leu Ile Tyr  His Glu Ile Leu Asn
2785                2790                2795                2800

Ala Ile Glu Cys Arg  Cys Ser Pro Arg Lys  Cys Ser Lys
            2805                2810

<210> SEQ ID NO 3
<211> LENGTH: 60
<212> TYPE: DNA
<213> ORGANISM: Canine

<400> SEQUENCE: 3 aggggtttc caaaatgaca aaagagtgag cctctccgtg tatctcggag a attttcga          60

<210> SEQ ID NO 4
<211> LENGTH: 60
<212> TYPE: DNA
<213> ORGANISM: Canine

<400> SEQUENCE: 4
cattcatttg tttgtcaatg gtaccatgct gcaggggacc caaaggtaag t cagaagccc         60

<210> SEQ ID NO 5
<211> LENGTH: 60
<212> TYPE: DNA
<213> ORGANISM: Canine

<400> SEQUENCE: 5
gaatgttcag gttaatatgg accctgggga tcactttgca accccttgt t ttttcagat         60
```

```
<210> SEQ ID NO 6
<211> LENGTH: 60
<212> TYPE: DNA
<213> ORGANISM: Canine

<400> SEQUENCE: 6
gagggagccg gggcccagag acaggaagta aatgtgccca gggaaagtga g tggcaggac     60

<210> SEQ ID NO 7
<211> LENGTH: 60
<212> TYPE: DNA
<213> ORGANISM: Canine

<400> SEQUENCE: 7
tgggtgaaag cccccatatcc cgactcctgg tcaaggagac tttgcaccaa g gtcccagcc   60

<210> SEQ ID NO 8
<211> LENGTH: 60
<212> TYPE: DNA
<213> ORGANISM: Canine

<400> SEQUENCE: 8
ctggagcatg gggttggggt tggaaggtgg agggacatgg aggaaatgca t gagaagcac    60

<210> SEQ ID NO 9
<211> LENGTH: 58
<212> TYPE: DNA
<213> ORGANISM: Canine

<400> SEQUENCE: 9
gcttcctgag ctcctccttg tcccaccagc atctccatgc cctacgcctc c aatgggc     58

<210> SEQ ID NO 10
<211> LENGTH: 24
<212> TYPE: DNA
<213> ORGANISM: Canine

<400> SEQUENCE: 10
aaatgacaaa agagtgagcc ggtc                                            24

<210> SEQ ID NO 11
<211> LENGTH: 24
<212> TYPE: DNA
<213> ORGANISM: Canine

<400> SEQUENCE: 11
aagtctcctt gaccagcggt cggg                                            24

<210> SEQ ID NO 12
<211> LENGTH: 35
<212> TYPE: PRT
<213> ORGANISM: Canine

<400> SEQUENCE: 12

Gly Gly Phe Gln Asn Asp Lys Arg Val Ser L eu Ser Val Tyr Leu Gly
  1               5                  10                 15

Glu Phe Phe Asp Ile His Leu Phe Val Asn G ly Thr Met Leu Gln Gly
                20                  25                 30

Thr Gln Arg
        35

<210> SEQ ID NO 13
```

```
<211> LENGTH: 9
<212> TYPE: PRT
<213> ORGANISM: Canine

<400> SEQUENCE: 13

Ile Ser Met Phe Tyr Ala Ser Asn Gly
 1               5
```